(12) United States Patent
Nishio et al.

(10) Patent No.: US 9,126,270 B2
(45) Date of Patent: Sep. 8, 2015

(54) DEVICE FOR DETECTING TOOL TIP POSITION OF REMOTE-CONTROLLED ACTUATOR

(75) Inventors: Yukihiro Nishio, Iwata (JP); Yoshitaka Nagano, Iwata (JP)

(73) Assignee: NTN CORPORATION, Osaka (JP)

( * ) Notice: Subject to any disclaimer, the term of this patent is extended or adjusted under 35 U.S.C. 154(b) by 785 days.

(21) Appl. No.: 13/390,600

(22) PCT Filed: Aug. 19, 2010

(86) PCT No.: PCT/JP2010/063976
§ 371 (c)(1),
(2), (4) Date: Feb. 15, 2012

(87) PCT Pub. No.: WO2011/024696
PCT Pub. Date: Mar. 3, 2011

(65) Prior Publication Data
US 2012/0143203 A1  Jun. 7, 2012

(30) Foreign Application Priority Data
Aug. 27, 2009 (JP) ................................. 2009-196660

(51) Int. Cl.
*G01B 5/30* (2006.01)
*B23B 39/14* (2006.01)
(Continued)

(52) U.S. Cl.
CPC ............ *B23B 39/14* (2013.01); *A61B 17/1631* (2013.01); *A61B 19/5244* (2013.01); *G01B 5/30* (2013.01); *A61B 17/1668* (2013.01); *A61B 2019/2211* (2013.01); *A61B 2019/464* (2013.01); *A61B 2019/466* (2013.01); *A61B 2019/467* (2013.01); *A61B 2019/502* (2013.01);

(Continued)

(58) Field of Classification Search
CPC .......... G01B 5/30; A61B 17/14; A61B 10/18
USPC ................ 73/760; 600/106, 424, 300; 606/96
See application file for complete search history.

(56) References Cited

U.S. PATENT DOCUMENTS 4,265,231 A   5/1981   Scheller, Jr. et al.
4,466,429 A   8/1984   Loscher et al.
(Continued)

FOREIGN PATENT DOCUMENTS

EP   0 364 057    10/1989
JP   2004-97790    4/2004
(Continued)

OTHER PUBLICATIONS

Japanese Office Action mailed Sep. 24, 2013 in corresponding Japanese Application No. 2009-196660.
(Continued)

*Primary Examiner* — Lisa Caputo
*Assistant Examiner* — Nigel Plumb

(57) ABSTRACT

A tool tip position detecting device for a remote controlled actuator having an elongated spindle guide, a tool fitted to a tip thereof and a main body housing having a base end of the spindle guide connected thereto. The device includes an external force free position detector for detecting the tip position of the tool from a detection value thereof, a strain detector for detecting a strain of the spindle guide, and a corrector for correcting the tip position of the tool, which has been detected by the external force free position detector, with the use of a detected strain value of the strain detector.

15 Claims, 23 Drawing Sheets

(51) Int. Cl.
*A61B 17/16* (2006.01)
*A61B 19/00* (2006.01)

(52) U.S. Cl.
CPC . *A61B2019/5255* (2013.01); *A61B 2019/5261* (2013.01)

(56) References Cited

U.S. PATENT DOCUMENTS

| | | | |
|---|---|---|---|
| 5,249,581 | A | 10/1993 | Horbal et al. |
| 6,434,507 | B1 * | 8/2002 | Clayton et al. ................ 702/152 |
| 6,887,247 | B1 * | 5/2005 | Couture et al. ................. 606/96 |
| 7,166,114 | B2 | 1/2007 | Moctezuma De La Barrera et al. |
| 7,273,483 | B2 * | 9/2007 | Wiener et al. ................. 606/169 |
| 8,105,346 | B2 | 1/2012 | Nakanishi |
| 2004/0098006 | A1 * | 5/2004 | Nakanishi ..................... 606/170 |
| 2004/0152955 | A1 * | 8/2004 | McGinley et al. ............ 600/300 |
| 2004/0171929 | A1 * | 9/2004 | Leitner et al. ................. 600/424 |
| 2005/0177168 | A1 * | 8/2005 | Brunnett et al. ................ 606/80 |
| 2006/0258938 | A1 * | 11/2006 | Hoffman et al. .............. 600/424 |
| 2006/0263744 | A1 | 11/2006 | Nakanishi |
| 2007/0066917 | A1 * | 3/2007 | Hodorek et al. .............. 600/595 |
| 2007/0151390 | A1 | 7/2007 | Blumenkranz et al. |
| 2007/0208252 | A1 * | 9/2007 | Makower ..................... 600/424 |
| 2007/0265653 | A1 | 11/2007 | Suzuki |
| 2008/0039746 | A1 * | 2/2008 | Hissong et al. .................... 601/3 |
| 2008/0249395 | A1 | 10/2008 | Shachar et al. |
| 2009/0143642 | A1 * | 6/2009 | Takahashi et al. ............ 600/106 |

FOREIGN PATENT DOCUMENTS

| | | |
|---|---|---|
| JP | 2004-521684 | 7/2004 |
| JP | 2004-237092 | 8/2004 |
| JP | 2005-523067 | 8/2005 |
| JP | 2005-328971 | 12/2005 |
| JP | 2007-301149 | 11/2007 |
| JP | 2009-131374 | 6/2009 |
| WO | WO 02/063236 A2 | 8/2002 |
| WO | WO 03/088852 A1 | 10/2003 |
| WO | WO 2005/077284 A2 | 8/2005 |

OTHER PUBLICATIONS

International Search Report for PCT/JP2010/063976 mailed Nov. 16, 2010.

International Preliminary Report on Patentability mailed Mar. 22, 2012 issued in corresponding International Patent Application No. PCT/JP2010/063976.

Extended European Search Report issued May 11, 2015 in corresponding European Patent Application No. 10811746.6.

* cited by examiner

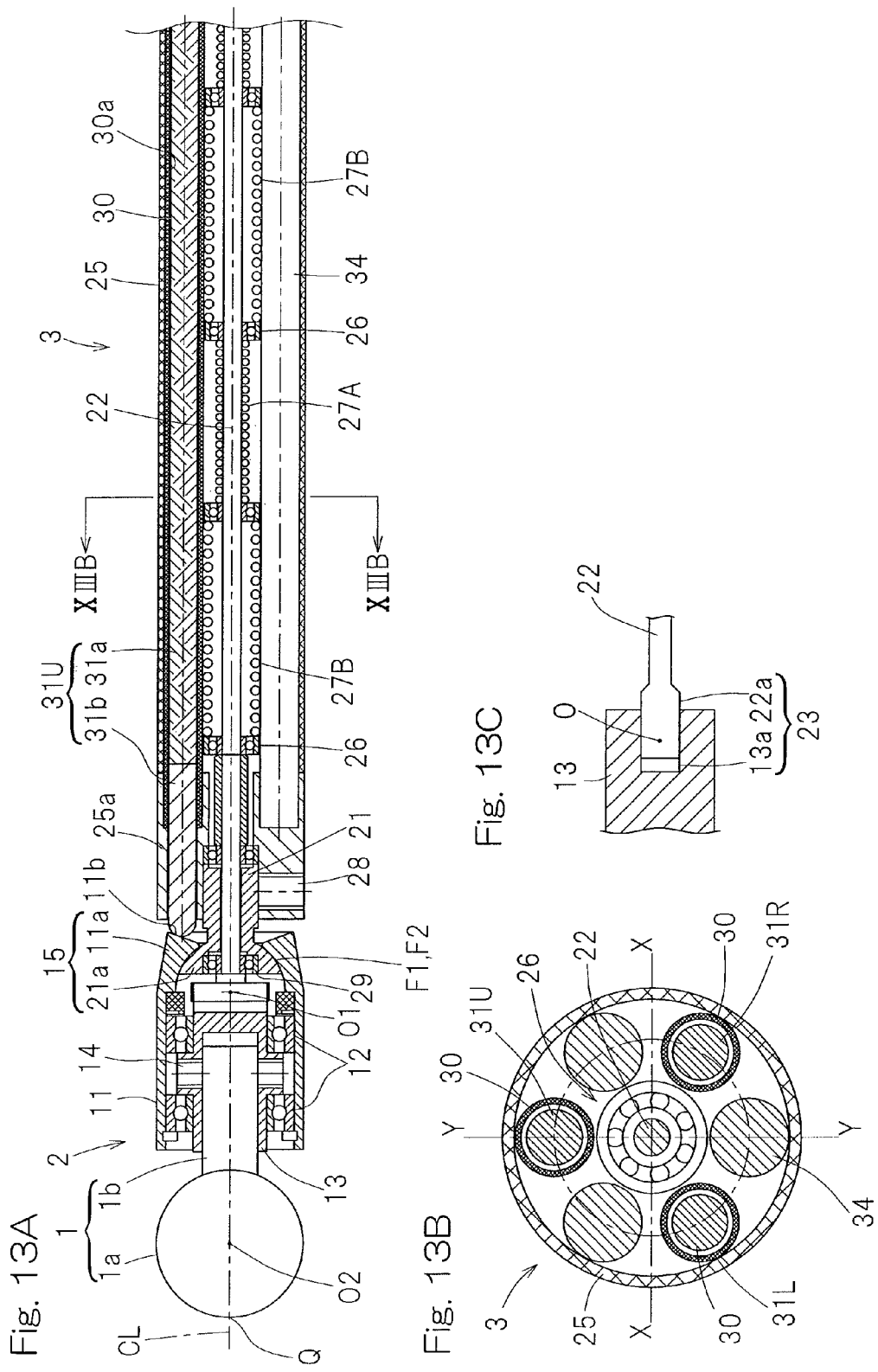

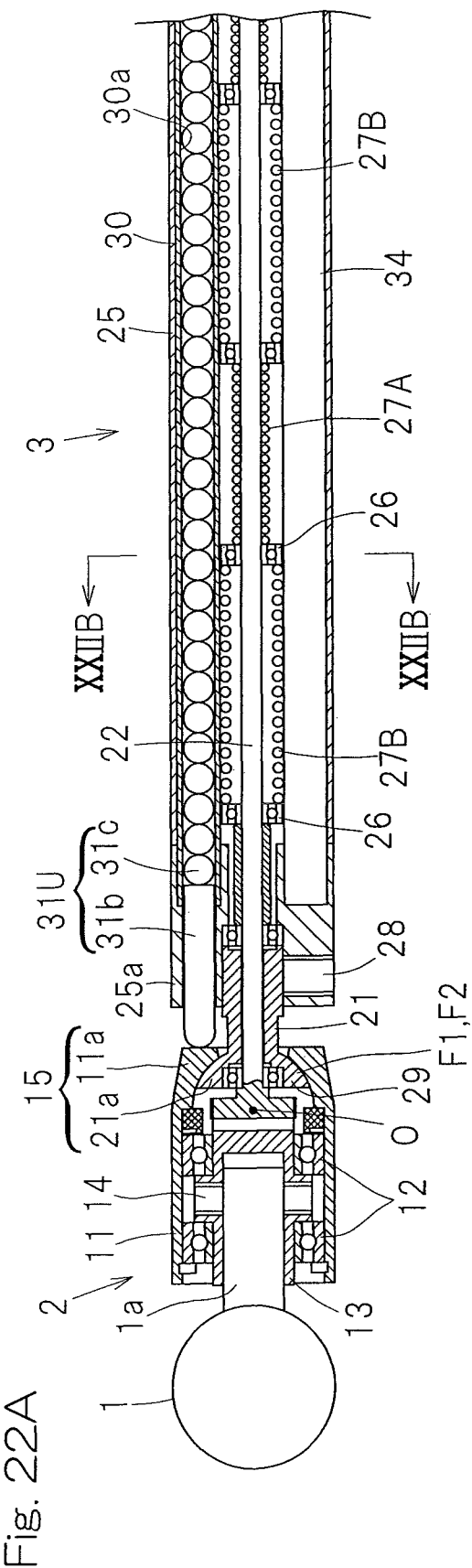
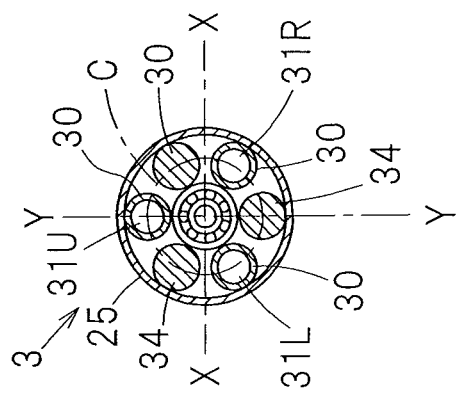
Fig. 22A
Fig. 22B

DEVICE FOR DETECTING TOOL TIP POSITION OF REMOTE-CONTROLLED ACTUATOR

CROSS REFERENCE TO RELATED APPLICATIONS

This application claims the benefit under 35 U.S.C. Section 371, of PCT International Application No. PCT/JP2010/063976, filed Aug. 19, 2010, which claimed priority to Japanese Application No. 2009-196660, filed Aug. 27, 2009 in the Japanese Patent Office, the disclosures of which are hereby incorporated by reference.

BACKGROUND OF THE INVENTION

1. Field of the Invention

The present invention relates to a navigation system for a remote controlled actuator of a kind, which is used in medical and mechanical processing applications and capable of altering the attitude of a machine tool by remote control.

2. Description of Related Art

Remote controlled actuators are currently available; some are used in the medical field for osteo treatment and some are used in the mechanical processing field for drilling and cutting a bone. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip join replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a drive transmitting means disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet with this desire, the following technique has hitherto been suggested. For example, the Patent Document 2 listed below discloses the elongated pipe having its intermediate portion curved double to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated 180°.

If in a condition, in which the artificial joint is inserted into an artificial joint insertion hole formed in the living bone, a large gap exist between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever the pipe take any shape, the working range of the tool is limited by the shape of the pipe and, therefore, it is difficult to widen the working range of the tool to process the artificial joint insertion hole so that the living bone and the artificial joint may can have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

Where the artificial joint insertion hole is to be processed in the bone with the use of the remote controlled actuator, it is quite often that the tool cannot be directly viewed with eyes and, therefore, a tool tip position detecting device is needed in order to detect the tip position of the tool. As a method to measure a position of a bone which is an object to be processed, the following techniques have hitherto been well known in the art.

The Patent Document 4 listed below discloses the navigation system, in which a marker is applied to the bone so that the position of the bone can be measured by the detection of the marker with the use of an optical sensor. Using this technique, when a marker is applied not only to the bone, but also to the body of a remote controlled actuator, which is a stationary portion of such actuator, respective positions of the bone and the actuator main body can be measured.

The Patent Document 5 also listed below discloses the navigation system, in which a marker, which is formed in a specific pattern, not in a dot, is applied to the remote-controlled actuator main body so that both of the position of the marker and the attitude of the remote-controlled actuator main body to which the marker has been applied can be detected by the detection of the pattern of that marker with the use of a marker detecting unit. Once the attitude of the remote-controlled actuator main body is determined, the tip position of the tool can be estimated from the relative positional relation between the tip position of the tool and the site of the remote-controlled actuator main body where the marker has been applied. It is, however, to be noted that the relative positional relation between the tip position of the tool and the site of the remote-controlled actuator main body where the marker has been applied is measured beforehand and is recorded and stored as a positional relational information.

It occurs quite often that the tool is replaced with a different type thereof depending on an object to be processed and/or upon, for example, wear, and, therefore, the positional relational information to be used in estimation of the tip position of the tool is needed to be updated each time the replacement takes place. As such the Patent Document 5 discloses the use of a switch operatively linked with removal of the tool to provide a piece of information with which the operator of the remote controlled actuator can be informed of the necessity of updating of the positional relational information.

The Patent Document 6 listed below discloses the navigation system, in which a second marker different from a first marker fitted to the remote controlled actuator main body is prepared for use and in which the tip end of the tool is brought into contact with the second marker and, using a positional relation between the remote-controlled actuator main body and the second marker then measured, the tip position of the tool is estimated on the basis of the positional relation between the remote-controlled actuator main body and the first marker measured during the procedure.

PRIOR ART LITERATURE

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] U.S. Pat. No. 5,249,581
[Patent Document 5] U.S. Pat. No. 6,434,507
[Patent Document 6] U.S. Pat. No. 7,166,114

In the conventional measuring methods hereinabove described, although no fitting site of the remote controlled actuator main body, to which the marker is fitted, is specifically defined, fitting of the marker directly to the tool is practically impossible to achieve and, considering that the pipe section is replaced in dependence on, for example, the type of the tool and/or the object to be processed, the marker is usually fitted to a main body housing to which the base end of the pipe section is connected. However, by the effect of a cutting resistance, which acts on the base end of the pipe section, and an external force, which is received when the pipe section collides a peripheral part of the site of cutting, the pipe section, which is of an elongated shape, tends to flexure. The greater the length of the pipe section, the larger the amount of flexure thereof. Where the marker is fitted to the main body housing, by the effect of flexure of the pipe section as discussed above, it will become difficult to accurately estimate the tip position of the tool, thus posing a problem that the processing accuracy may be reduced.

SUMMARY OF THE INVENTION

The present invention is aimed at providing a tool tip position detecting device which is effective to detect the tip position of the tool accurately at all times by estimating accurately a displacement of the tip position of the tool, which has resulted from the flexure of a spindle guide, relative to a remote controlled actuator provided with the tool at a tip of the spindle guide having an outer shell of a pipe-like shape and of an elongated shape.

A remote controlled actuator 5 of the present invention is explained with the aid of reference numerals employed in the accompanying drawings, which shows preferred embodiments of the present invention, for the purpose of facilitating a better understanding of the present invention. A tool tip position detecting device 53 for the actuator includes a spindle guide 3 of an elongated shape, a main body housing 4 to which a base end of the spindle guide 3 is connected, a tool 1 rotatably supported by a tip end of the spindle guide 3, a tool rotation drive source 41 for rotating the tool 1 through a drive transmitting unit 22 inserted within the spindle guide 3, and an operator unit 51 for performing an operation of the tool rotation drive source 41. The actuator 5 also includes an external force free position detector 54 operable to detect the position and the attitude of the main body housing 4 and also to detect from a detection value thereof, the tip position of the tool 1, when no external force is applied to the tool 1 and the spindle guide 3, strain detectors 60, 62X and 62Y for detecting a strain induced in the spindle guide 3, and a corrector 55 for correcting the tip position of the tool 1, detected by the external force free position detector 54, with the use of respective detected strain values of the strain detectors 60, 60X and 60Y. It is to be noted that the external force free position detector 54 may detect the tip position of the tool 1 when external force is applied on the spindle guide 3, but a detection value outputted therefrom has to be represented by a value when no external force is applied.

According to the above described construction, the external force free position detector 54 detects the position and the attitude of the main body housing 4 and also detects, from a detection value thereof, the tip position of the tool 1 when no external force is applied to the tool 1 and the spindle guide 3. Also, the strain detectors 60, 62X and 62Y detect the strain induced in the spindle guide 3. The corrector 55 makes use of the detected strain values of the strain detectors 60, 62X and 62Y to correct the position of the tool 1 detected by the external force free position detector 54. Accordingly, a displacement of the tip position of the tool 1, which is brought about by flexure of the spindle guide 3, is corrected and the accurate tip position of the tool 1 is therefore detected.

The remote controlled actuator 5 performs a cutting of, for example, a bone by the rotation of the tool 1 provided at the tip of the spindle guide 3. Since the tool 1 is rotated by the tool rotation drive source 41 through the drive transmitting unit 22 inserted within the spindle guide 3, the rotation of the tool 1 can be operated by remote control.

In the present invention, in order to enable the use in a plurality of different models of remote controlled actuators 5, which make use of respective different types of spindle guides 3, the corrector 55 may include a plurality of type specific tables 55aA, 55aB, . . . for storing relations between the detected strain values of the strain detectors 60, 62X and 62Y and the amounts of correction used in the correction referred to above, for each of the types of the spindle guides 3, a table selector 55b for selecting out from the type specific tables 55aA, 55aB, . . . one of the type specific tables 55aA, 55aB, . . . for each type of the spindle guide 3.

Where a certain remote controlled actuator 5 is to be used, the type specific table 55aA, 55aB, . . . , which corresponds to the type of the spindle guide 3 used in such remote controlled actuator 5 is selected by the table selector 55b. From the relation between the detected strain value and the amount of correction, which are stored in the selected type specific table 55aA, 55aB, . . . , the amount of correction appropriate to the detected strain value is selected. By so doing, the proper amount of correction appropriate to the detected strain value of the strain detectors 60, 62X and 62Y can be determined even relative to one of the plurality of remote controlled actuators 5 employing different types of spindle guides 3, respectively.

In the present invention, the external force free position detector 54 may include a marker detecting unit 8 for detecting a position and an attitude of a marker 7A fitted to the main body housing 4, a relative position storage unit 83 for storing relative positions of a tip of the tool 1 relative to the marker 7A, and an estimating unit 85 for estimating the tip position of the tool 1 from the position and the attitude of the marker 7A, detected by the marker detecting unit 8, and the relative positions of the tip of the tool 1 relative to the marker 7A stored in the relative position storage unit 83.

According to the above described construction, the marker detecting unit 8 detects the position and the attitude of the marker 7A fitted to the main body housing 4. Accordingly, the position of the main body housing 4, at which the marker is fitted, and the attitude of the main body housing 4 are detected. From the result of detection performed by the marker detecting unit 8 and the relative position of the tip of the tool 1 relative to the marker 7A stored in the relative position storage unit 83, the estimating unit 85 estimates the tip position of the tool 1.

The strain detectors 62X and 62Y can have a strain sensor 60 fitted to the spindle guide 3. In such case, the strain sensor 60 is preferably fitted to four or more axially same positions on an outer peripheral surface of the spindle guide 3 in a fashion circumferentially spaced from each other.

By fitting the strain sensor 60 to the spindle guide 3, the strain of the spindle guide 3 can be detected with the strain detectors 62X and 62Y. If the strain sensor 60 is fitted to four or more portions held at different locations in the circumferential direction, the strain of the spindle guide in two axis directions can be detected with the two strain sensors 60 taken as a pair. The strain sensor 60 forming a part of the strain detectors 62X and 62Y may be said to be a strain detector by itself.

The strain sensor may be a strain gauge. The strain gauge is inexpensive and can be easily fitted to the spindle guide.

The strain sensor referred to above may be a sensor utilizing an optical fiber. For the sensor utilizing the optical fiber, a distributed optical fiber sensor and a Fiber Bragg Grating sensor (FBG), for example, are known. Of them the FBG is capable of dynamically and highly accurately measuring a localized strain and can also be used in a manner similar to the manner of use of the conventional strain gauge.

The strain detectors 62X and 62Y are operable to transmit an output of the strain sensor 60 in the form of an electrical signal to a control system portion of the tool tip position detecting device 53. If the output of the strain sensor 60 is transmitted to the control system portion of the tool tip position detecting device 53 in the form of the electrical signal, where the spindle guide 3 provided with the strain sensor 60 and the control system portion of the tool tip position detecting device 53 are distant from each other, information transmission therebetween can be facilitated.

It is recommended to use a correction determiner 65 for receiving a signal indicative of an operating condition of an instruments 67 and/or 68, which is likely to form a noise generating source against the strain sensor 60, and for outputting an alarming command signal in the event that the signal indicates the instruments 67 and/or 68 being operated, and an alarming unit 66 for outputting an alarm in response to the alarming command signal of the correction determiner 65.

Where the remote controlled actuator 5 is, for example, for use in the medical treatment, it is quite often that instruments tending to emit electromagnetic waves such as, for example, the medical electrosurgical knife 67 and the ultrasonic coagulation and dissection instrument 68 are positioned in the vicinity of the remote controlled actuator 5. The electromagnetic waves emitted from those instruments will possibly become noises to the strain sensors 60 of the remote controlled actuator 5, which deal with feeble signals. Although in general the medical electrosurgical knife 67 and the ultrasonic coagulation and dissection instrument 68 will not be used simultaneously with the remote controlled actuator 5, an erroneous activation of one or both of the medical electrosurgical knife 67 and the ultrasonic coagulation and dissection instrument 68 while the remote controlled actuator 5 is in use will result in an error contained in the detection of the tool tip position by the tool tip position detecting device 53. In order to avoid this problem, the use is made of the correction determiner 65 and the alarming unit 66 so that when the signal indicative of the medical electrosurgical knife 67 and/or the ultrasonic coagulation and dissection instrument 68 being activated is inputted to the correction determiner 66, the correction determiner 65 generates the alarming command signal to cause the alarming unit 66 to issue the alarm. By so doing, the operator can be informed that correction of the tip position of the tool 1 set by the corrector 55 is not correct. Also, it is possible to refrain the tip position of the tool 1, detected at that time, from being used in various operation controls of the remote controlled actuator 5.

Alternatively, the use may be made of an inspecting strain sensor 70 separate from the strain sensor 60 and insensible to an external force applied to the spindle guide 3, a correction determiner 72 for receiving an output value of the inspecting strain sensor 70 or a processed value of the output value which has been applied with a predetermined signal processing and for outputting an alarming command signal in the event that the value thereof exceeds a predetermined threshold value, and an alarming unit 66 for outputting an alarm in response to the warning command signal of the correction determiner 72.

The inspecting strain sensor 70 is not affected by the external force acting on the spindle guide 3, and accordingly, in the event that the output value of the inspecting strain sensor 70 or the output value in which the predetermined signal processing has been applied exceeds the threshold value, it may be thought that the electromagnetic waves generated by the medical electrosurgical knife 67 and/or the ultrasonic coagulation and dissection instrument 68 are treated as noises. In other words, it means that the medical electrosurgical knife 67 and/or the ultrasonic coagulation and dissection instrument 68 is/are being activated. Accordingly, in the event that the value referred to above exceeds the predetermined threshold value, the correction determiner 72 outputs the alarming command signal to cause the alarming unit 66 to issue the alarm. By so doing, in a manner similar to that described hereinabove, the operator can be informed that the correction of the tip position of the tool 1 set by the corrector 55 is improper. Also, it is possible to refrain the tip position of the tool 1, so detected at that time, from being used in various operational controls of the remote controlled actuator 5.

In the event that the correction determiners 65 and 72 output the alarming command signal, the corrector 55 preferably performs a correction with the use of a detected strain value of the strain detector 60, 62X and 62Y immediately before the correction determiner 65 and 72 outputs the warning command signal. By allowing the corrector 55 to perform the correction with the use of the detected strain value of the strain detectors 60, 62X and 62Y immediately before the correction determiners 65 and 72 output the alarming command signal, the correction with the use of the detected strain values of the strain detectors 60, 62X and 62Y as updated as possible can be performed while the possibility of the error, which would result from the detection of the noises of the strain sensors 60, is eliminated.

In the present invention, the use may be made of a display unit 56 for displaying one or both of an image and position information on a screen and a display information generator 57 for displaying, on the screen, information on the tip position of the tool, which has been estimated by the external force free position detector 54 and subsequently corrected by the corrector 55. The use of the display unit 56 and the display information generator 57 is effective to allow information on the tip position of the tool 1 to be displayed on the screen of the display unit 56. Accordingly, the operator can properly handle the remote controlled actuator 5 while looking at the information on the tip position of the tool 1 then displayed on the screen of the display unit 56.

In the present invention, the spindle guide may include a spindle guide main body and a distal end member fitted to a tip of the spindle guide main body through a distal end member connecting structure for alteration in attitude, in which case the distal end member rotatably supports the tool and the use is made of an attitude altering drive source for altering the attitude of the distal end member through an attitude altering member inserted within the spindle guide main body and an attitude altering unit for operating the attitude altering drive source. According to this construction, if the spindle guide is made up of the spindle guide main body and the distal end member and the attitude of the distal end member is altered by means of the attitude altering source through the attitude altering member inserted within the spindle guide main body, the attitude of the tool can be altered by remote control. If the attitude of the tool is changeable, regardless of the shape of the spindle guide, the tool can be retained at a proper attitude and processing of a complicated and delicate hole such as, for example, an artificial joint insertion hole can be relatively easily and accurately carried out.

Where the distal end member of the spindle guide referred to above is changeable in attitude, the distal end member rotatably may support a spindle for holding the tool, a rotation of the tool rotation drive source being transmitted to the spindle through the drive transmission unit and in which the attitude altering member has a flexibility and is inserted in a guide hole having its opposite end opening, the attitude of the distal end member being altered by selectively advancing or retracting the attitude altering member by means of a drive of the attitude altering drive source with the tip held in contact with the distal end member. If the attitude altering member is advanced or retracted by means of the attitude altering drive source, the tip of the attitude altering member acts on the distal end member to alter the attitude of the distal end member. Since the attitude altering member is passed through a guide hole, there is no possibility that the attitude altering member may displace in position in a direction perpendicular to the lengthwise direction, and it acts on the distal end member properly at all times and the attitude altering operation of the distal end member is accomplished accurately. Also, since the attitude altering member has a flexibility, the attitude altering operation takes place assuredly even if the spindle guide is in a condition being curved.

Also, where the distal end member of the spindle guide is alterable in attitude, the distal end member rotatably may support a spindle for holding the tool, a rotation of the tool rotation drive source being transmitted to the spindle through the drive transmission unit and in which the attitude altering member is a wire and is inserted in a guide hole having its opposite end opening, the attitude of the distal end member being altered by selectively advancing or retracting the attitude altering member by means of a drive of the attitude altering drive source in a condition with the tip held in direct or indirect contact with the distal end member. Even with this construction, the attitude of the distal end member is altered by means of advance or retraction of the attitude altering member in a manner similar to that described hereinbefore. In the case of this construction, with the attitude altering member being employed in the form of the wire, the assured advancing or retracting operation of the attitude altering member and a sufficient flexibility can be obtained.

Furthermore, where the distal end member of the spindle guide is alterable in attitude, the distal end member rotatably may support a spindle for holding the tool, a rotation of the tool rotation drive source being transmitted to the spindle through the drive transmission unit, in which case the attitude altering member is inserted in a guide hole having its opposite end opening, the attitude of the distal end member being altered by selectively advancing or retracting the attitude altering member by means of a drive of the attitude altering drive source in a condition with the tip held in direct or indirect contact with the distal end member, and in which the use may be made of a drive mechanism section within the main body housing for transmitting an operation of the attitude altering drive source to the attitude altering member. The drive mechanism section includes a screw mechanism having a male screw portion, formed in a base end of the attitude altering member, and a female screw portion fixed to the main body housing and meshed with the male screw portion. The attitude altering drive source is comprised of a rotary actuator, the attitude altering member being selectively advanced or retracted by an action of the screw mechanism when the base end of the attitude altering member is rotated by the rotary actuator.

Even in the construction described above, as is the case with the previously described construction, the attitude of the distal end member is altered by means of the advance or retraction of the attitude altering member. If any external force is applied to the tool or the distal end member, an axial force acts from the distal end member on the attitude altering member. However, since the attitude altering drive source is in the form of a rotary actuator and the attitude altering member is selectively advanced or retracted by the action of the screw mechanism by rotating the base end of the attitude altering member through the rotary actuator, no axial movement take place unless the attitude altering member rotates in a direction of rotation. For this reason, the attitude stability of the distal end member relative to the external force is good. Also, since the rotary actuator is used as the attitude altering drive source, it is sufficient to transmit a rotational output of this rotary actuator itself to the base end of the attitude altering member and the drive mechanism section for the attitude alteration can be simplified.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 13A is a longitudinal sectional view of the spindle guide of the remote controlled actuator;

FIG. 13B is a cross sectional view taken along the line XIIIB-XIIIB in FIG. 13A;

FIG. 13C is a diagram showing a connecting structure between a distal end member and a drive transmitting unit;

FIG. 22A is a longitudinal sectional view showing the tool and the spindle guide of the remote controlled actuator according to a fourth preferred embodiment of the present invention;

FIG. 22B is a cross sectional view taken along the line XXIIB-XXIIB in FIG. 22A:

DESCRIPTION OF PREFERRED EMBODIMENTS

Figure 1:
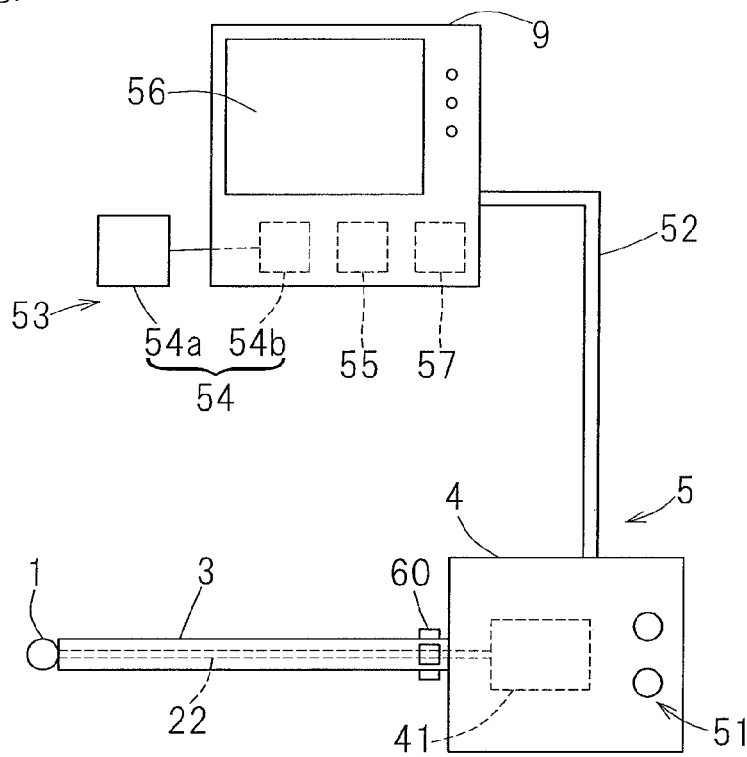
FIG. 1 is a diagram showing a schematic structure of a remote controlled actuator and a tool tip position detecting device therefor according to a first preferred embodiment of the present invention.

A first preferred embodiment of a remote controlled actuator provided with a tool tip position detecting device designed in accordance with the present invention is shown in FIG. 1. This remote controlled actuator, generally identified by 5, includes a main body housing 4, a spindle guide 3 of an elongated shape having a base end connected with the main body housing 4, and a tool 1 rotatably supported by a tip end of the spindle guide 3. A tool rotation drive source 41 is provided within the main body housing 4 and a rotation of the tool rotation drive source 41 is transmitted to the tool 1 through a drive transmission unit 22 inserted within the spindle guide 3. The tool rotation drive source 41 may, however, be provided outside the main body housing 4. The main body housing 4 is provided with the operator unit 51 for performing a switching on and off of the tool rotation drive source 41 and an adjusting operation of the rotational speed.

The main body housing 4 is connected with a computer 9 through a cable 52. The computer 9 includes an external force free position detector 54 and a corrector 55, both of which form respective parts of the tool tip position detecting device 53. More specifically, the external force free position detector 54 is made up of a detecting machine 54a of, for example, an optical system for detecting the position and the attitude of the main body housing 4, and a storing and calculating section 54b within the computer 9. The computer 9 also includes a display unit 56 and a display information generator 57 for generating information to be displayed on the display unit 56. The storing and calculating section 54b of the external force free position detector 54, the corrector 55 and the display information generator 57 are comprised of hardware of the computer 9 and respective programs executed thereby or comprised of them with an electronic circuit added thereto.

A strain sensor 60 for detecting a strain induced in the spindle guide 3 is fitted to an outer periphery of the base end of the spindle guide 3. In the instance as shown, four strain sensors 60 are fitted having been spaced 90° from each other in a circumferential direction. For the strain sensor 60, a strain gauge, for example, is employed. The strain gauge is inexpensive and can easily be fitted to the spindle guide 3.

Figure 2:
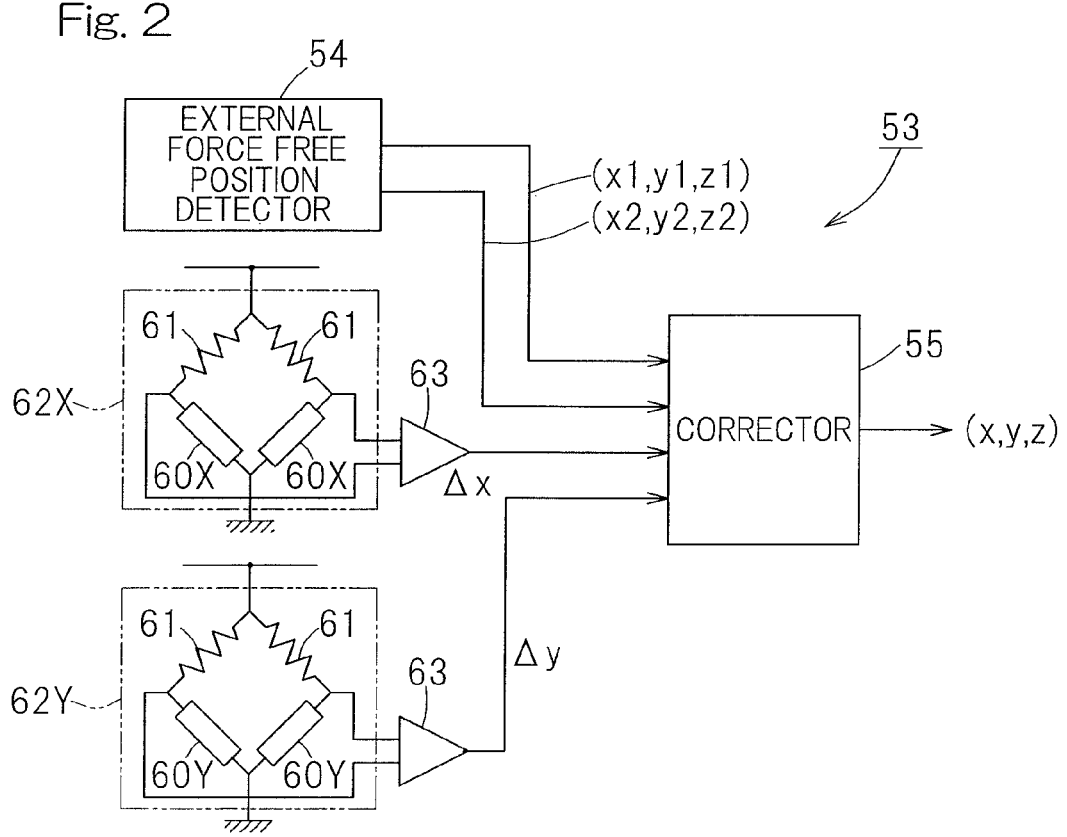
FIG. 2 is a block diagram showing a structure of the tool tip position detecting device for the remote controlled actuator.

FIG. 2 illustrates a block diagram showing the structure of the tool tip position detecting device 53. The external force free position detector 54 referred to previously detects the position and the attitude of the main body housing 4 by means of the detecting machine 54a (best shown in FIG. 1) and then determines from a detection value thereof, the tip position of the tool 1 when external force acts on the tool 1 and the spindle guide 3. It is to be noted that the external force free position detector 54 may detect the tip position of the tool 1 when external force acts on the spindle guide 3, but a detection value outputted therefrom has to be a value when no external force is applied. For the detecting machine 54a, other than that of the optical system, that of an electromagnetic system or the like can be employed. Signals representative of X-, Y- and Z-axis positions (x1, y1, and z1) of the main body housing 4, which are determined by the external force free position detector 54, and signals representative of X-, Y- and Z-axis positions (x2, y2, and z2) of the tool 1, which are also determined by the external force free position detector 54, are supplied to the corrector 55.

The four strain sensors 60 referred to previously are such that two of them, which are opposed to each other, form a respective sensor pair and are therefore made up of two X-axis strain detection sensors 60X and two Y-axis strain detection sensors 60Y A pair of the X-axis strain detection sensors 60X are combined with two resistors 61 to form a bridge circuit. This bridge circuit is a strain detector 62X for detecting the X-axis strain occurring in the spindle guide 3. Similarly, another pair of the Y-axis strain detection sensors 60Y are combined with two resistors 51 to form a bridge circuit. This bridge circuit is a strain detector 62Y for detecting an Y-axis strain occurring in the spindle guide 3. The strain sensors 60 forming a part of the strain detectors 62X and 62Y can be said to be nothing other than the strain detector. Respective detected strain values Δx and Δy of those strain detectors 62X and 62Y are, after having been amplified by associated amplifiers 63, supplied to the corrector 55. An output of the strain sensor 60 is supplied to a control system portion of the tool tip position detecting device 53, which is provided within the computer 9, in the form of an electric signal through the cable 52, and accordingly, even if the spindle guide 3, where the strain sensors 60 are provided, and the computer 9 are positioned having been separated from each other such as in the embodiment now under discussion, information transmission therebetween is easy to achieve.

Figure 3:
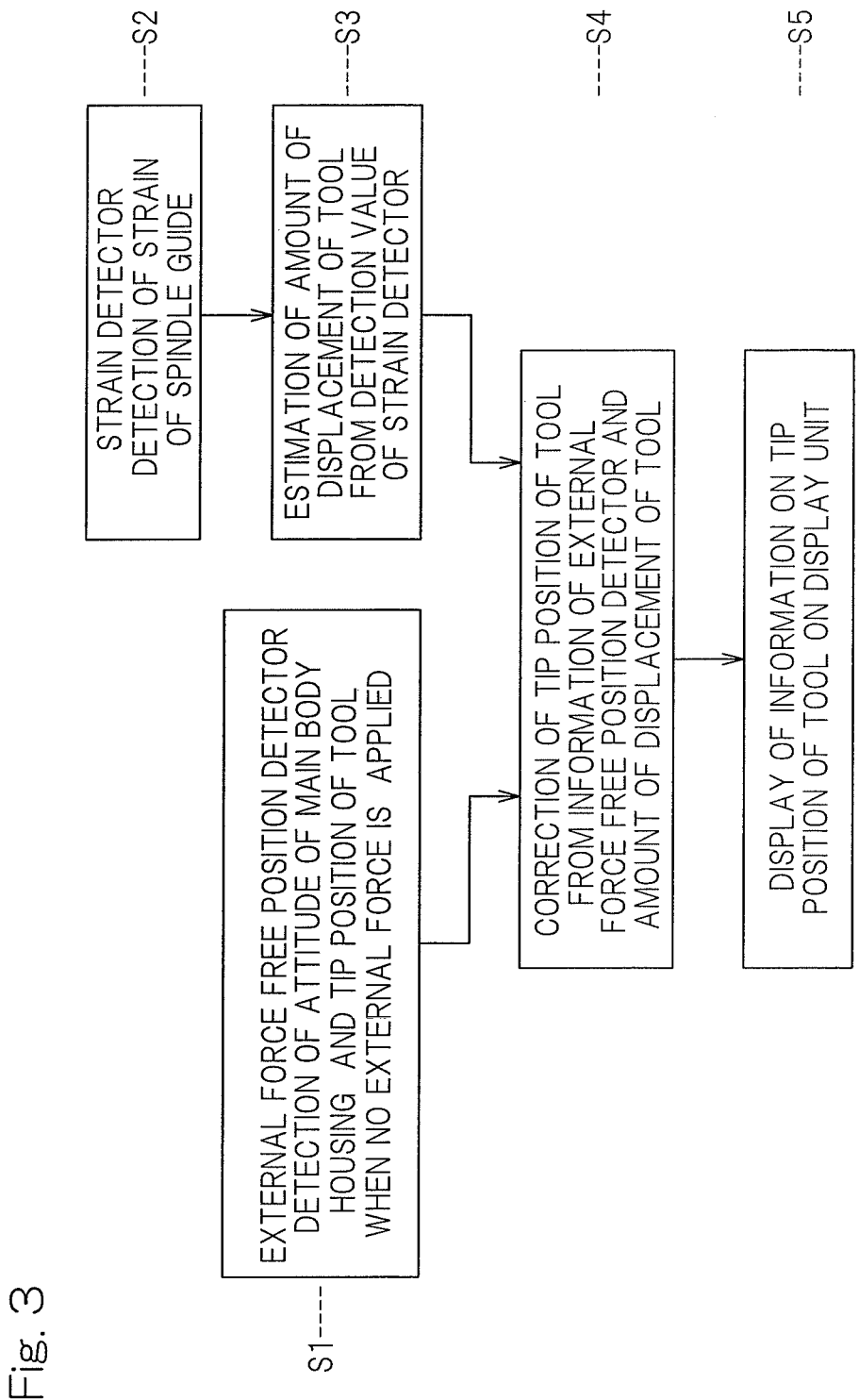
FIG. 3 is a flow chart showing the sequence of control of the tool tip position detecting device.

The corrector 55 performs respective processes at a third step S3 and a fourth step S4, both being shown in the flow chart of control by the tool tip position detecting device shown in FIG. 3. Specifically, at the third step S3, from the detected strain values Δx and Δy of the strain detectors 62X and 62Y, the amount of displacement of the tip position of the tool 1, which is brought about by flexure of the spindle guide 3, is estimated. At the fourth step S4, relative to the tip position (x2, y2 and z2) of the tool 1 detected by the external force free position detector 54 when no external force is applied, a correction process is performed by adding the amount of displacement referred to above in a direction in dependence on the attitude of the main body housing 4. In this way, the displacement of the tip position of the tool 1 resulting from the flexure of the spindle guide 3 is corrected and the accurate tip position (x, y and z) of the tool 1 (FIG. 2) can be obtained. At a fifth step S5, the tip position (x, y and z) of the tool 1 so obtained is supplied to the display information generator 57 (FIG. 1) at which it is processed to suitable numerical values or graphic representations or the like, which are in turn displayed on a screen of the display unit 56 (FIG. 1).

Figure 4:
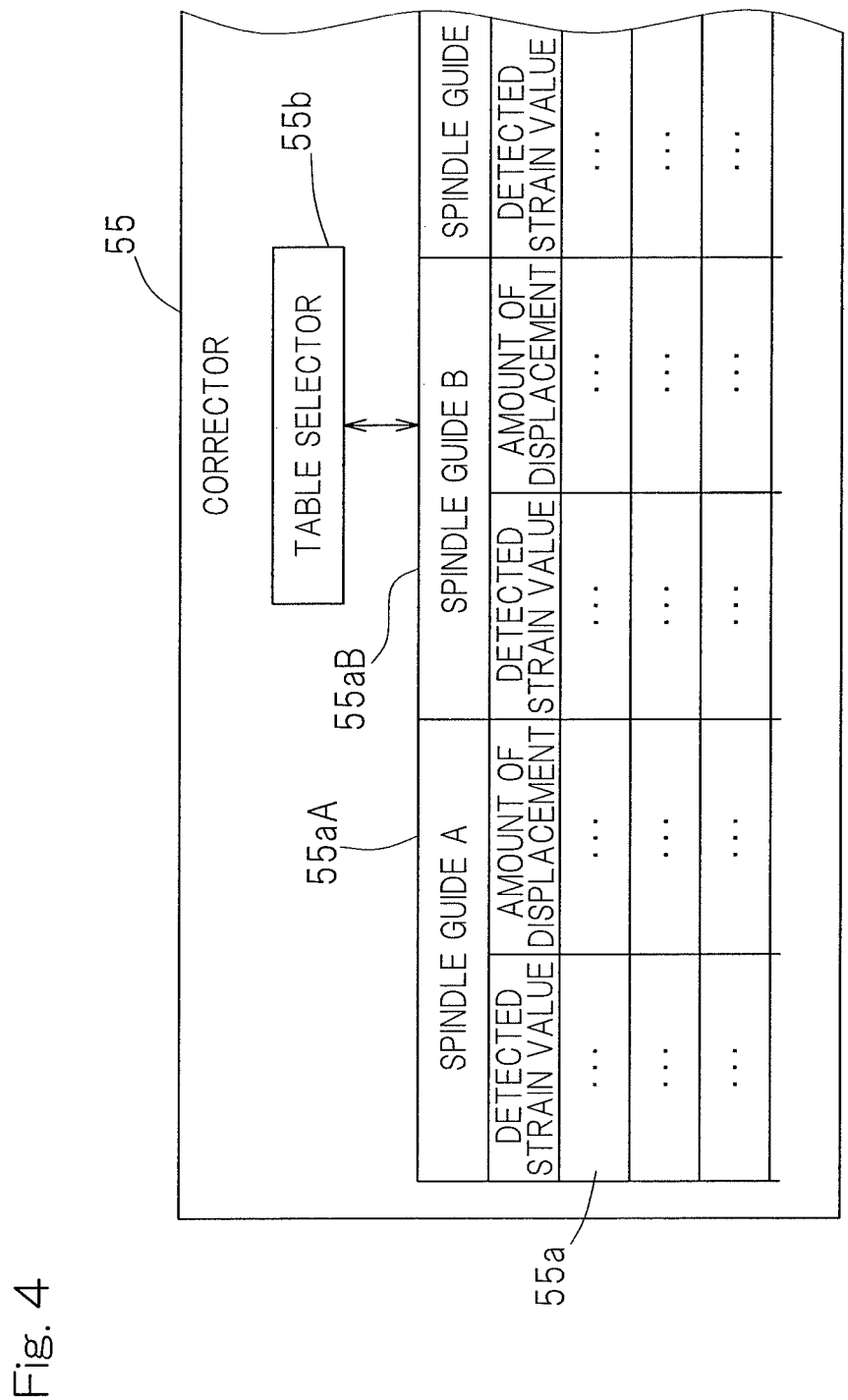
FIG. 4 is a diagram showing a structure of a portion of a corrector employed in the tool tip position detecting device.
Figure 5A:
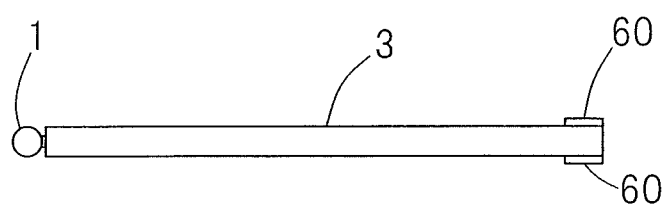
FIG. 5A is a diagram showing a spindle guide of the remote controlled actuator in a normal condition.
Figure 5B:
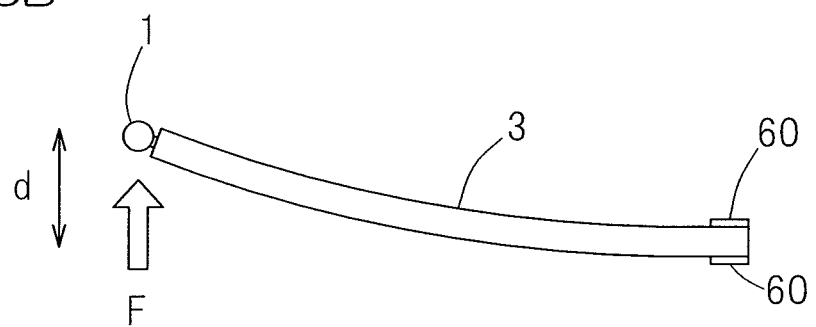
FIG. 5B is a diagram showing the spindle guide in a condition in which an external force is applied thereon.

The amount of displacement of the tip position of the tool 1 discussed hereinabove is estimated in the following manner. By way of example, assuming that the condition in which no external force is applied to the tool 1 and the spindle guide 3 is shown in FIG. 5A, when an external force F acting in a direction perpendicular to the lengthwise direction of the spindle guide 3 is applied to the tool 1 or the tip end of the spindle guide 3, the spindle guide 3 will flexes as shown in FIG. 5B and the tip position of the tool 1 is displaced a distance d. At this time, the train sensor 60 in the form of a strain gauge positioned on the flexing side of the spindle guide 3 (on an upper side of the drawing showing the spindle guide 3) contracts, but the strain sensor 60 positioned on a contracting side (or a lower side of the drawing) elongates. Accordingly, in dependence on the flexure of the spindle guide 3, the detected strain values Δx and Δy of the strain detectors 62X and 62Y differ from each other. Relations between the detected strain values Δx and ΔY and the amount of displacement of the tool 1 are determined beforehand by means of a series of experiments and/or simulations and those relations are then recorded and stored in a table 55a as shown in FIG. 4. In the event that the detected strain values Δx and Δy are outputted, the detected strain values Δy and Δy are checked against the contents recorded in the table 55a and, accordingly, the amount of displacement in the tip position of the tool 1 can be estimated.

In the example as shown in FIG. 4, the table 55a is comprised of a plurality of type specific tables 55aA, 55aB, . . . , and for each type of the spindle guide 3, the relations between the detected strain values Δx and Δy and the amounts of displacement of the tool 1 are recorded and stored in the type specific tables 55aA, 55aB, . . . . Where a certain remote controlled actuator 5 is to be used, one of the type specific tables 55aA, 55aB, . . . , which corresponds to the type of the spindle guide 3 used in such remote controlled actuator 5, is selected by the table selector 55b. From the relation between the detected strain values Δx and Δy and the amount of correction, both stored in the selected type specific table 55aA, 55aB, . . . , the amount of correction appropriate to the detected strain values Δx and Δy is selected. By so doing, even for the different types of the remote controlled actuators 5 employing the different types of the spindle guides 3, respectively, the amount of correction appropriate to the detected strain values Δx and Δy of the strain detectors 62X and 62Y can be determined. The table selector 55b performs the above described selection in accordance with an input from, for example, an input unit (not shown) of the computer 9, which is introduced as a result of an inputting operation by an operator.

A method of processing, for example, a bone with this remote controlled actuator 5 will now be described with reference to FIG. 1. When the tool rotation drive source 41 is driven, the rotational force thereof is transmitted to the tool 1 through the drive transmitting unit 22, resulting in a rotation of the tool 1. By the effect of the rotating tool 1, the bone or the like is cut. On and off switching, as well as a rotational speed adjusting operation, of the rotation of the tool 1 are accomplished by the operator unit 51 by remote control. During the processing, since information on the accurate tip position of the tool 1 is displayed on the display unit 56, it is possible to perform a proper operation on the basis of the information that can be obtained from the display unit 56.

While the strain gauge has been described as employed for the strain sensor 60 in the embodiment of the present invention as hereinabove described, the strain sensor 60 may be in the form of a sensor utilizing an optical fiber. For the strain detecting sensor of a type utilizing the optical fiber, a distributed optical fiber sensor and a Fiber Bragg Grating sensor (FBG), for example, are known. Of them, the FBG is capable of measuring a localized strain highly accurately and dynamically and can be utilized in a manner similar to the conventional strain gauge.

Figure 6:
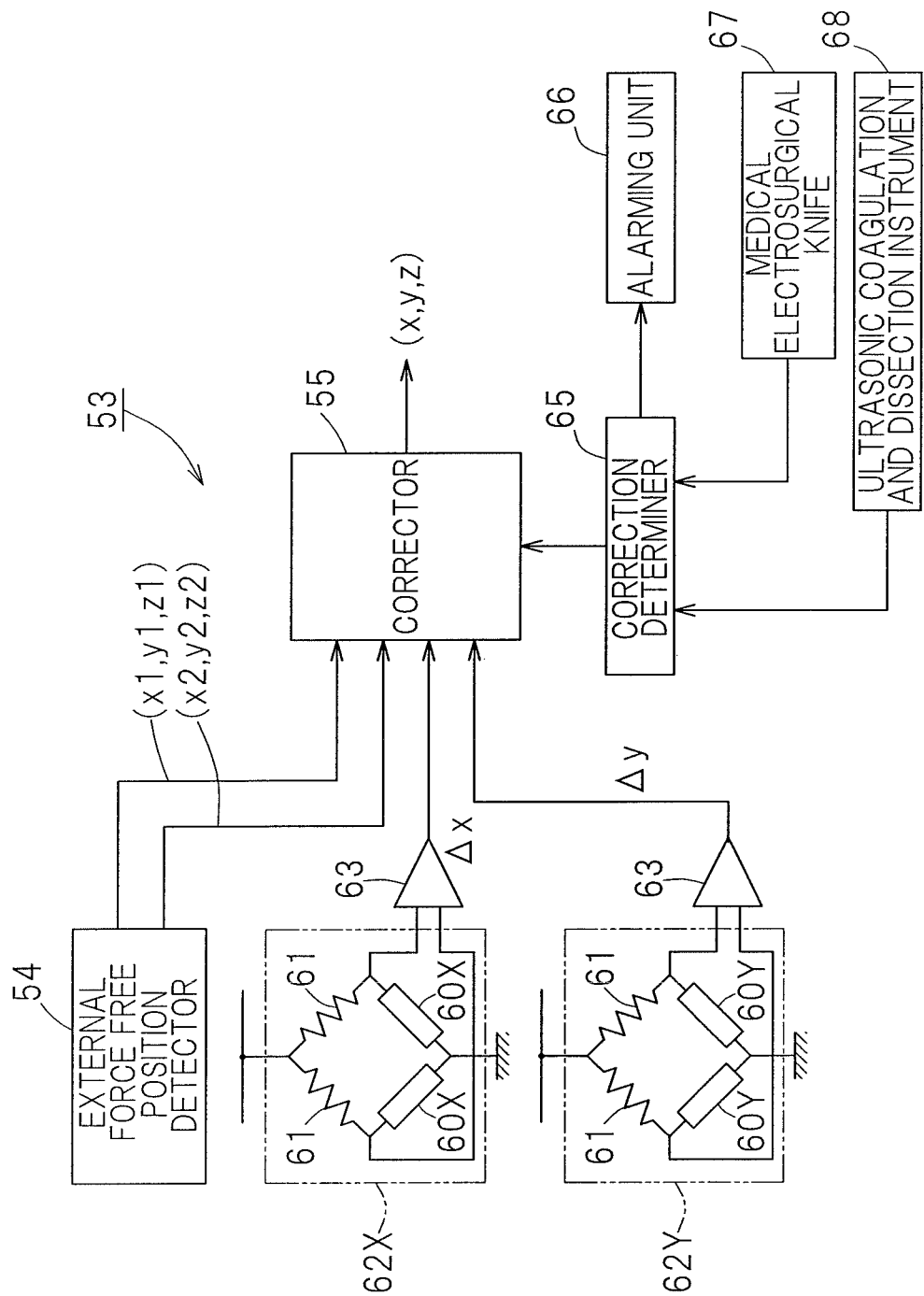
FIG. 6 is a block diagram showing a structure of a different tool tip position detecting device.

FIG. 6 illustrates a block diagram showing the tool tip position detecting device which is different from the example shown in and described with particular reference to FIG. 2. This tool tip position detecting device 53 includes, in addition to the various structural features of the tool tip position detecting device shown in and described with reference to FIG. 2, a correction determiner 65, connected with the corrector 55, and an alarming unit 66 connected with the correction determiner 65. The correction determiner 65 is comprised of hardware of the computer 9 and a program executable thereby or comprised of them with an electronic circuit added thereto. This correction determiner 65 is connected with an instrument, which would possibly form a source of generation of noises of the strain sensor 60, for example, an medical electrosurgical knife 67 and an ultrasonic coagulation and dissection instrument 68 in the instance as shown, and, based on respective signals indicative of operating conditions that are fed from those instruments, the correction determiner 65 determines whether or not the correction accomplished by the corrector 55 is proper. The alarming unit 66 issues an alarm to the operator by means of sounds, light and/or a screen display on the display unit 56.

Figure 7:
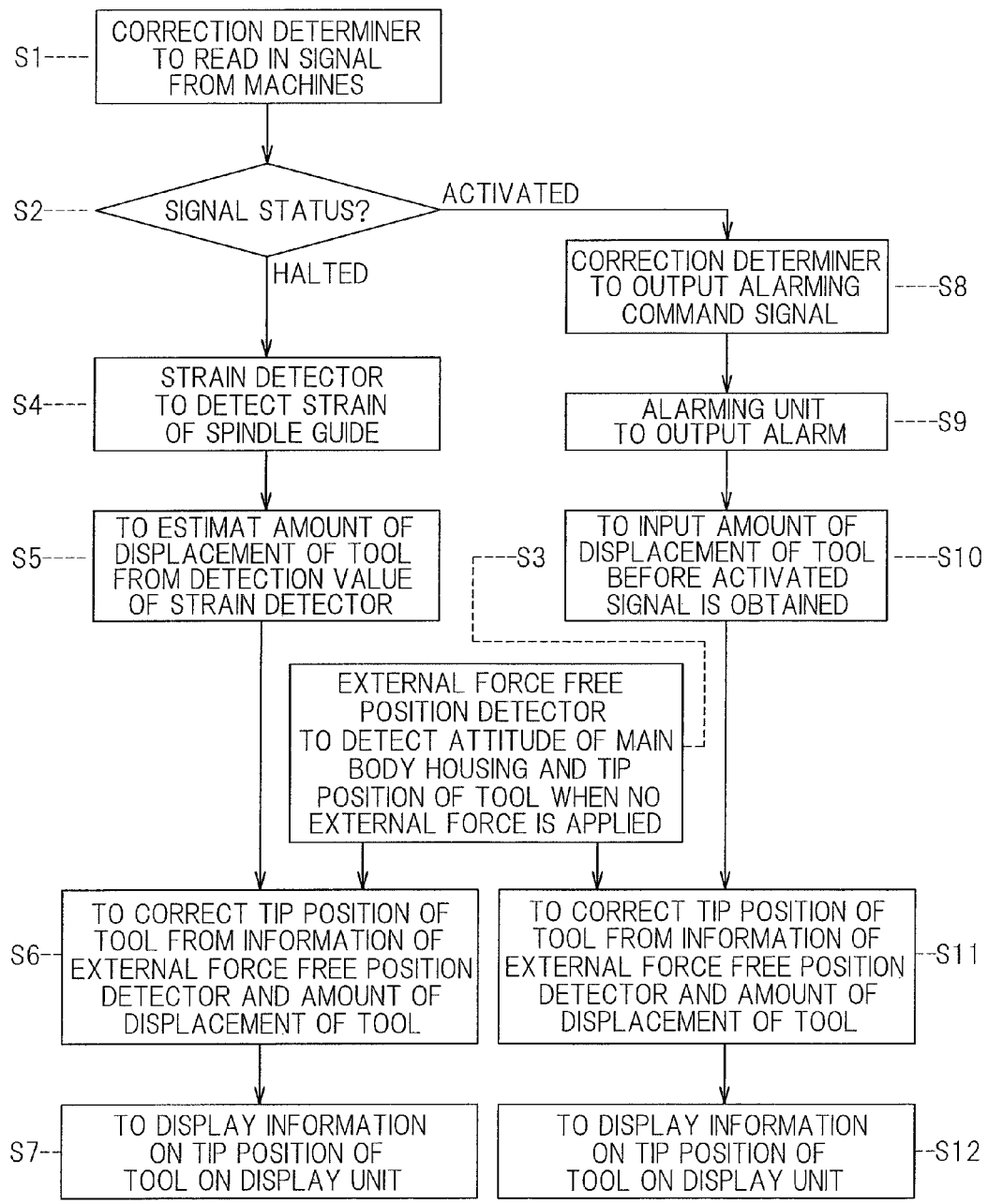
FIG. 7 is a flow chart showing the sequence of control of the tool tip position detecting device.

As shown in the flow chart shown in FIG. 7, the correction determiner 65 reads in the signals indicative of the operating conditions of the medical electrosurgical knife 67 and the ultrasonic coagulation and dissection instrument 68 at step S1 and, in the event that both of the medical electrosurgical knife 67 and the ultrasonic coagulation and dissection instrument 68 are then held at a halt as determined at step (S2), the program flow goes to the next succeeding step. In a manner similar to that described above, the corrector 55 performs the correction at step S6 to the tip position of the tool 1, which is detected by the external force free position detector 54 when no external force is applied, from the attitude of the main body housing 4, detected by the detecting unit 54, and the amount of displacement of the tip position of the tool 1 determined from the detected strain values Δx and Δy detected by the strain detectors 62X and 62Y.

In the event that one or both of the medical electrosurgical knife 67 and the ultrasonic coagulation and dissection instrument 68 is/are being activated as determined at step S2, the correction determiner 65 outputs an alarming command signal at step S8. Accordingly, the alarming unit 66 issues an alarm at step S9. In the event that the correction determiner 65 outputs the alarming command signal, the corrector 55 performs a correction at steps S10 and S11 with the use of the detected strain values Δx and Δy immediately before the correction determiner 65 issues the alarming command signal.

Where, by way of example, the remote controlled actuator 5 is used for medical, it is quite often that instruments tending to emit electromagnetic waves such as, for example, the medical electrosurgical knife 67 and the ultrasonic coagulation and dissection instrument 68 are positioned in the vicinity of the remote controlled actuator 5. The electromagnetic waves emitted from those instruments will possibly become noises to the strain sensors 60 of the remote controlled actuator 5, which deal with feeble signals. Although in general the medical electrosurgical knife 67 and the ultrasonic coagulation and dissection instrument 68 will not be used simultaneously with the remote controlled actuator 5, an erroneous activation of one or both of the medical electrosurgical knife 67 and the ultrasonic coagulation and dissection instrument 68 while the remote controlled actuator 5 is in use will result in an error contained in the detection of the tool tip position by the tool tip position detecting device.

In view of the above, in the event that the medical electrosurgical knife 67 and/or the ultrasonic coagulation and dissection instrument 68, which will possibly form a source of generation of noises, is/are in activation, the correction determiner 65 issues the alarming command signal to cause the alarming unit 66 to issue the alarm. By so doing, it is possible to inform the operator that the correction of the tool tip position performed by the corrector 55 is improper. Also, in the event that the correction determiner 65 outputs the alarming command signal, the corrector 55 performs the correction with the use of the detected strain values Δx and Δy immediately before the correction determiner 65 outputs the alarming command signal, and, accordingly, the correction with the use of the detected strain values Δx and Δy as updated as possible can be performed while the possibility of the error, which would result from the detection of the noises of the strain sensors 60, is eliminated.

Figure 8:
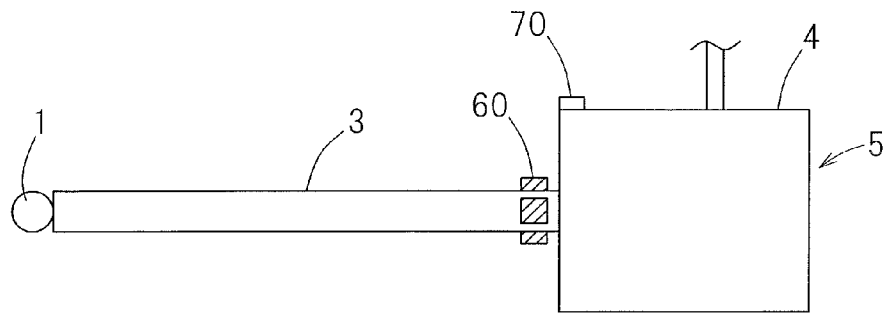
FIG. 8 is a diagram showing a schematic structure of the remote controlled actuator and the tool tip position detecting device therefor according to a second preferred embodiment of the present invention.
Figure 9:
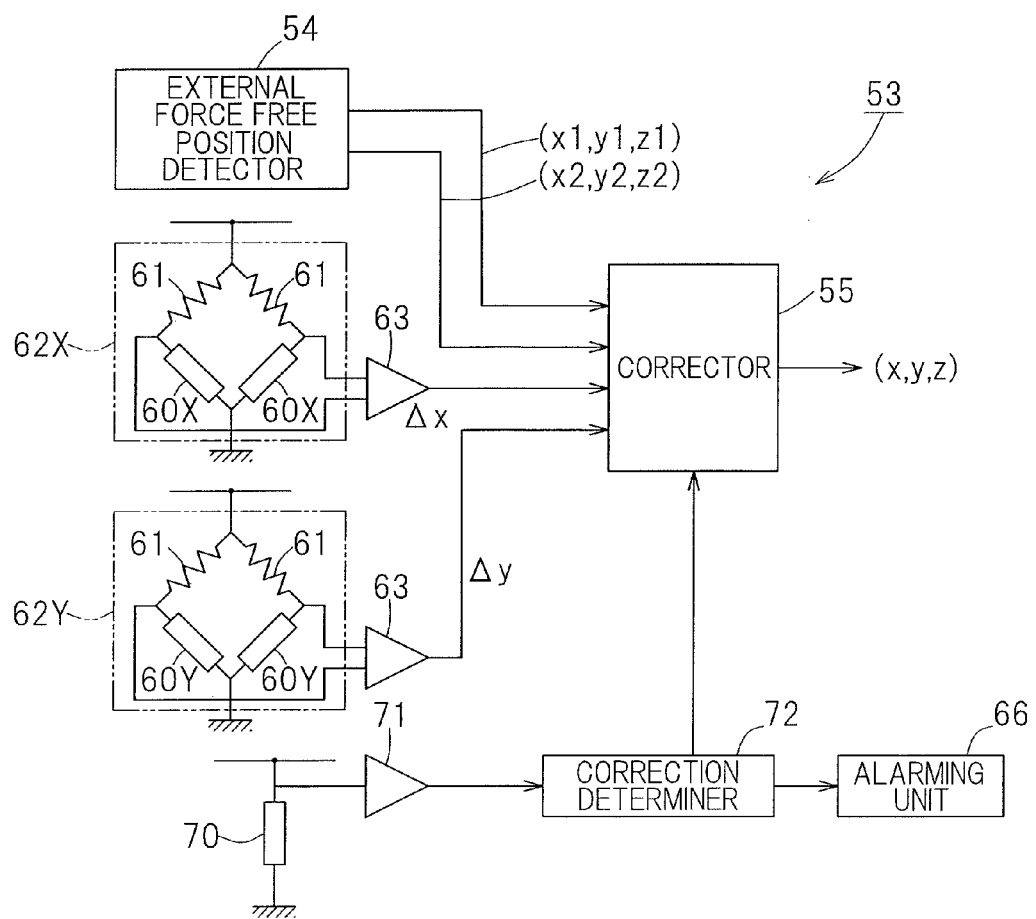
FIG. 9 is a block diagram showing a structure of the tool tip position detecting device for the remote controlled actuator.

FIG. 8 illustrates a second preferred embodiment of the remote controlled actuator provided with the tool tip position detecting device designed in accordance with the present invention and FIG. 9 illustrates a block diagram showing the schematic structure of the tool tip position detecting device therefor. As best shown in FIG. 8, the tool tip position detecting device 53 makes use of a dummy inspecting strain sensor 70, in addition to the strain sensors 60 for detecting the strains induced in the spindle guide 3. The inspecting strain sensor 70 is provided at a site which will not be affected by the external force applied to the spindle guide 3, such as, for example, the main body housing 4.

As shown in FIG. 9, a detection value of the inspecting strain sensor 70 is, after having been amplified by an amplifier 71, supplied to a correction determiner 72. This correction determiner 72 is also comprised of hardware of the computer 9 and a program executable thereby or comprised of them with an electronic circuit added thereto, as is the case with the previously described correction determiner 65. The correction determiner 72 determines that the correction performed by the corrector 55 is proper in the event that an output value of the inspecting strain sensor 70 or a value equivalent to the output value thereof to which a predetermined signal processing has been applied falls within a predetermined threshold value, but the previously described correction is improper in the event that it exceeds the threshold value. Since the inspecting strain sensor 70 is not affected by the external force applied to the spindle guide 3, in the event that the output value of the inspecting strain sensor 70 or the value equivalent to this output value to which the predetermined signal processing has been applied exceeds the threshold value, it is suspected that the electromagnetic waves generated by the medical electrosurgical knife 67 and/or the ultrasonic coagulation and dissection instrument 68, both best shown in FIG. 6, are treated as noises. In other words, it means that the medical electrosurgical knife 67 and/or the ultrasonic coagulation and dissection instrument 68 are being activated. Accordingly, in the event that the previously described value exceeds the threshold value, it is determined that the correction performed by the corrector 55 is improper.

In the event that the determination has been made that the correction performed by the corrector 55 is improper, the correction determiner 72 outputs the alarming command signal to cause the alarming unit 66 to issue the alarm. Accordingly, in a manner similar to that described hereinbefore, it is possible to inform the operator that the correction of the tool tip position performed by the corrector 55 is not proper. Also, if the correction determiner 72 outputs the alarming command signal, the corrector 55 performs the correction with the use of the detected strain values $\Delta x$ and $\Delta y$ immediately before the correction determiner 72 outputs the alarming command signal, and, accordingly, the correction with the use of the detected strain values $\Delta x$ and $\Delta y$ as updated as possible can be performed while the possibility of the error, which would result from the detection of the noises of the strain sensors 60, is eliminated.

Figure 10A:
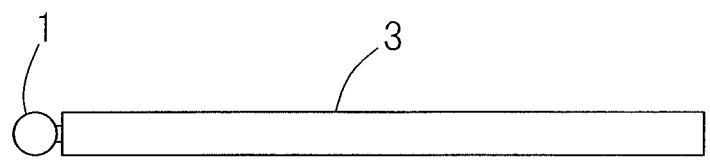
FIG. 10A is a diagram showing a spindle guide of the remote controlled actuator in a normal condition.
Figure 10B:
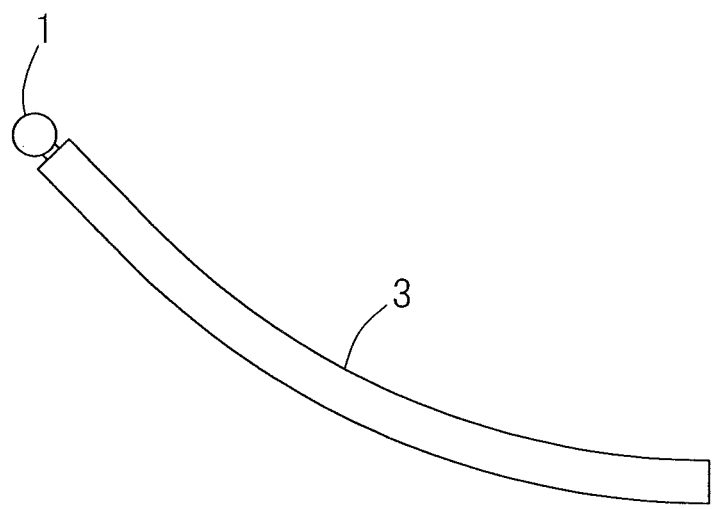
FIG. 10B is a diagram showing the spindle guide in a condition in which an external force is applied thereon.
Figure 11:
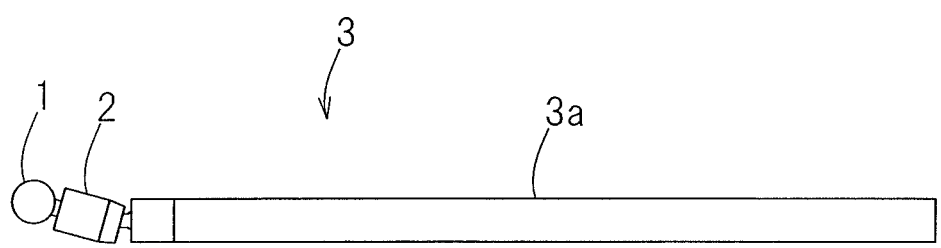
FIG. 11 is a diagram showing a different structure of the spindle guide.

The remote controlled actuator 5 according to the previously described embodiment of the present invention makes use of the spindle guide 3 of the linear shape as shown in FIG. 10A, but the spindle guide 3 may be of a curved shape as shown in FIG. 10B. Also, the structure is not necessarily limited to that in which the tool 1 is directly provided at the tip end of the spindle guide 3. By way of example, as shown in FIG. 11, the spindle guide 3 may be of a structure including a spindle guide main body 3a and a distal end member 2 fitted to a tip end of this spindle guide main body 3a for alteration in attitude, with the tool 1 rotatably supported by the distal end member 2. According to this structure, the attitude of the tool 1 can be freely changed to suit to the object to be processed.

Hereinafter, with reference to FIGS. 12 to 21, the remote controlled actuator, designed according to a third preferred embodiment of the present invention and having a capability of altering the attitude of the tool, and a navigation system therefor will be specifically described. The navigation system referred to hereinbefore and hereinafter means a system made up of a combination of the tool tip position detecting device 53 and a display device 80, best shown in FIG. 15, for displaying information obtainable from the tool tip position detecting device 53.

Figure 14A:
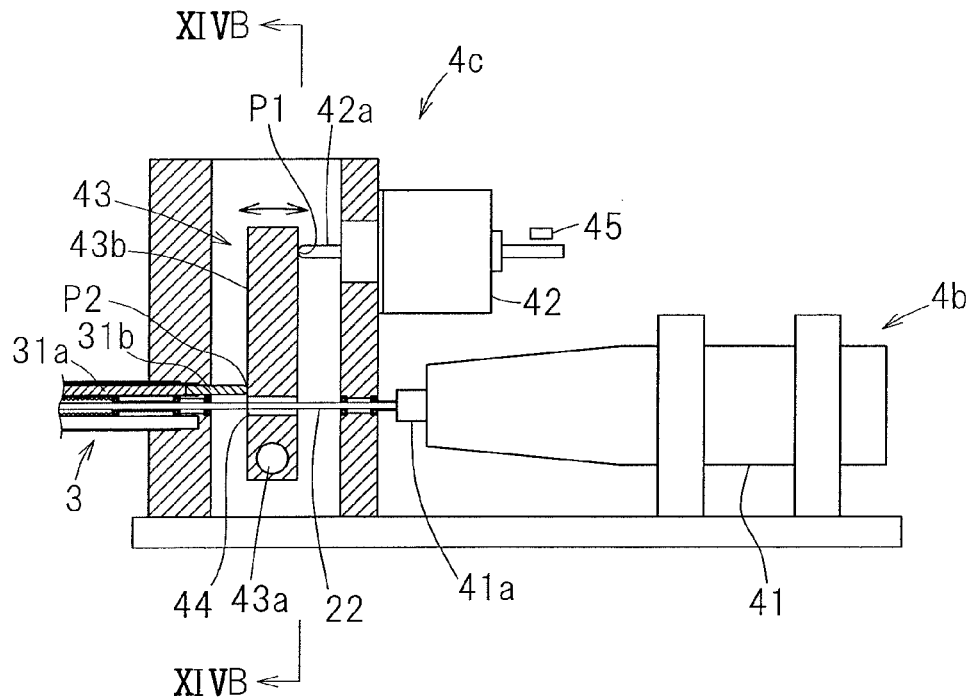
FIG. 14A is a fragmentary side sectional view showing, with a portion cut out, an attitude altering drive mechanism and a tool rotation drive mechanism, both employed in the remote controlled actuator.
Figure 14B:
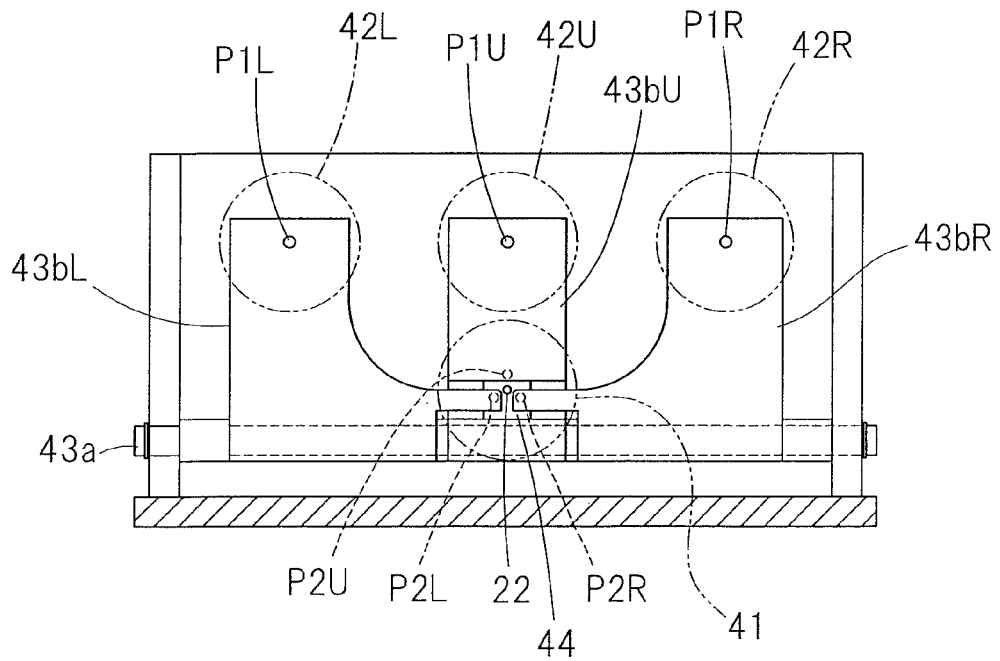
FIG. 14B is a cross sectional view taken along the line XIVB-XIVB in FIG. 14B.
Figure 15:
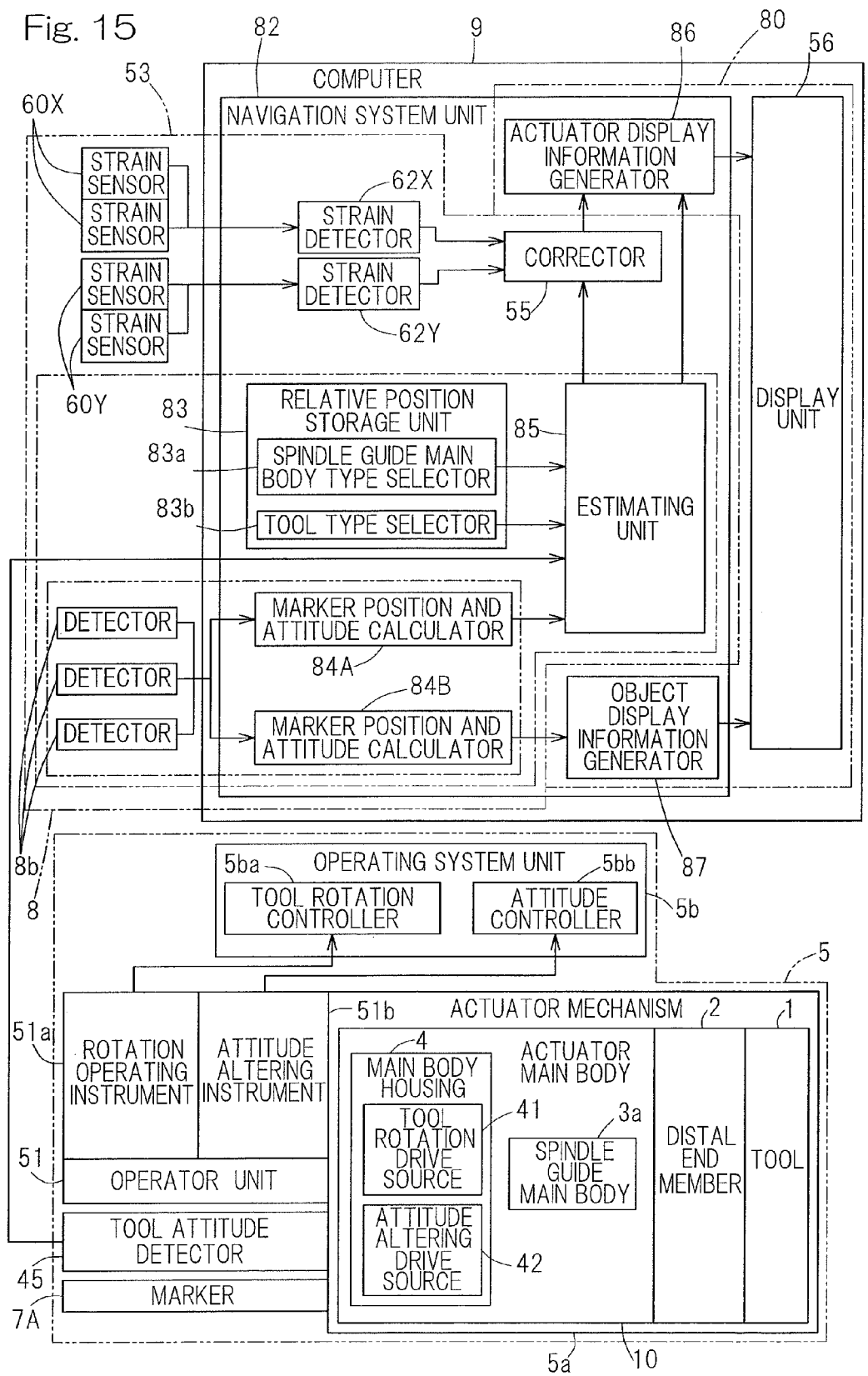
FIG. 15 is a block diagram showing a control system of the navigation system.

The remote controlled actuator 5 is comprised of an actuator mechanism section 5a, shown in FIGS. 13A to 13C and FIGS. 14A and 14B, and an operating system section 5b shown in FIG. 15. In FIG. 12 and FIGS. 13A to 13C, the spindle guide main body 3a is shown as having a linear shape, but the basic structure remains the same even if the spindle guide main body 3a has a curved shape.

Figure 12:
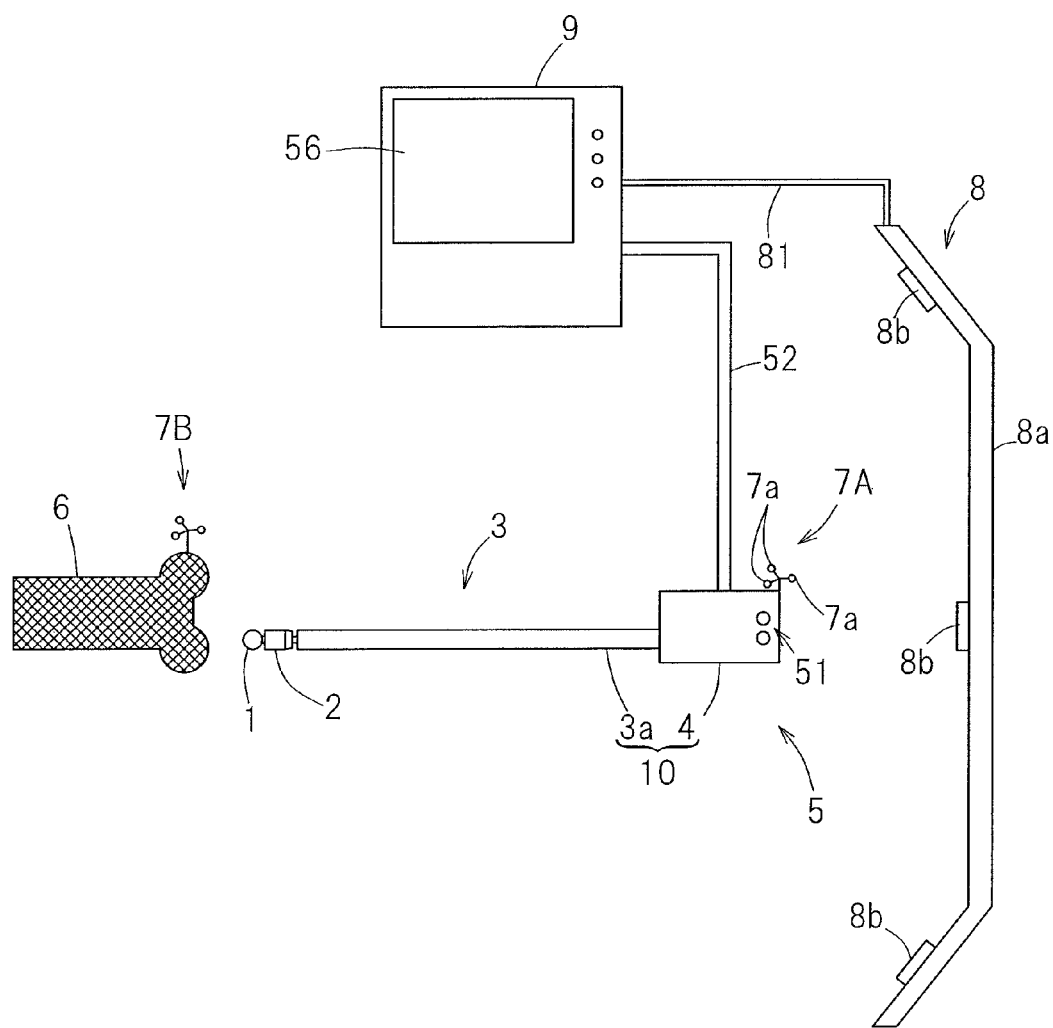
FIG. 12 is a diagram showing a schematic structure of the remote controlled actuator and a navigation system therefor according to a third preferred embodiment of the present invention.

Referring now to FIG. 12, the actuator mechanism 5a (FIG. 15) includes a distal end member 2 for holding a rotary tool 1, the elongated spindle guide main body 3a of a pipe-like appearance having its distal end to which the distal end member 2 is fitted for alteration in attitude, and a main body housing 4 to which a proximal end of the spindle guide section 3, opposite to the above mentioned distal end, is connected. The distal end member 2 and the spindle guide main body 3a cooperate with each other to define the spindle guide 3. The main body housing 4 builds in a tool rotation drive mechanism 4b (FIG. 14A) and an attitude altering drive mechanism 4c (FIG. 14A). Also, the spindle guide main body 3a and the main body housing 4 altogether constitute an actuator main body 10. The main body housing 4 is provided with an operator unit 51 that is made up of a rotation operating instrument 51a (FIG. 15), for rotating the tool 1 by controlling the operation of the tool rotation drive mechanism 4b and an attitude altering instrument or attitude operating unit 51b (FIG. 15), for effecting alteration of the attitude of the distal end member 2 by controlling the operation of the attitude altering drive mechanism 4c.

As shown in FIGS. 13A to 13C, the tool 1 is made up of the processing member 1a and a shank 1b. The processing member 1a is a tip portion of the tool 1. In the embodiment now under discussion, the processing member 1a is of a spherical shape. The distal end member 2 includes a generally or substantially cylindrical housing 1 and a spindle 13 rotatably accommodated within such cylindrical housing 11 through a pair of bearings 12. The spindle 13 is of a tubular shape having a distal side opening and having a hollow defined therein, and a tool 1 is drivingly coupled with the spindle 13. Specifically, a shank 1b of the tool 1 is inserted into the hollow of the spindle 13 in a removable fashion and is then coupled with such spindle 13 by means of a stop pin 14 for rotation together with the spindle 13. The distal end member 2 of the structure described above is coupled with a distal end of the spindle guide main body 3a through a distal end member connecting unit 15. The distal end member connecting unit 15 is means for supporting the distal end member 2 for displacement in attitude and is comprised of a spherical bearing. More specifically, the distal end member connecting unit 15 includes a guided member 11a in the form of an inner diameter reduced portion at a base end of the housing 11, and a guide member 21a in the form of a collar integral with a constraint member 21 fixed to the tip of the spindle guide main body 3a. The guided member 11a and the guide member 21a have respective guide faces F1 and F2 that are held in sliding contact with each other, and those guide faces F1 and F2 have respective centers of curvature lying at a point O1 on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered.

The spindle guide main body 3a includes a drive transmitting unit 22 for transmitting a rotational force exerted by a tool rotation drive source 41 accommodated within the main body housing 4 (FIG. 14A). In the illustrated example, the drive transmitting unit 22 is employed in the form of a wire capable of undergoing deformation to a certain extent. Material for the wire includes, for example, metal, resin or glass fiber. The wire may be either a single wire or a stranded wire. As best shown in FIG. 13C, the spindle 13 and the drive transmitting unit 22 are connected together by means of a universal joint 23 for transmitting rotation from the drive transmitting unit 22 to the spindle 13. The universal joint 23 is made up of a groove 13a, defined in a closed base end of the spindle 13, a projection 22a defined in a distal end of the drive transmitting unit 22 and engageable in the groove 13a. The center of joint between the groove 13a and the projection 22a is located at the same position as the centers of curvature O1 of the guide faces F1 and F2. The guide faces F1 and F2 are spherical surfaces having their centers lying at the center of pivot O1 and the distal end member 2 is tiltable in any arbitrary direction.

The spindle guide main body 3a includes an outer shell pipe 25 forming an outer shell of the spindle guide main body 3a and the drive transmitting unit 22 referred to above is positioned at the center of this outer shell pipe 25. The drive transmitting unit 22 so positioned is rotatably supported by a plurality of rolling bearings 26 positioned spaced a distant apart from each other in a direction axially of the spindle guide section 3. Spring elements 27A and 27B for generating a preload on the corresponding rolling bearing 26 are disposed between the neighboring rolling bearings 26. Each of those spring elements 27A and 27B is employed in the form of, for example, a compression spring. There are the spring element 27A for inner ring for generating the preload on the inner ring of the rolling bearing 26 and the spring element 27B for outer ring for generating the preload on the outer ring of the rolling bearing 26, and the both are arranged alternately relative to each other. The constraint member 21 referred to previously is fixed to a pipe end portion 25a of the outer shell pipe 25 by means of a fixing pin 28 and has its distal end inner peripheral portion supporting the distal end of the drive transmitting unit 22 through a rolling bearing 29. It is, however, to be noted that the pipe end portion 25a may be a member separate from the outer shell pipe 25 and may then be connected with the outer shell pipe 25 by means of, for example, welding.

Three guide pipes 30 open at opposite ends thereof is provided at circumferential positions lying between an inner diametric surface of the outer shell pipe 25 and the drive transmitting unit 22 and spaced 120° in phase from each other. Attitude altering members 31, each made up of a wire 31a and pillar shaped pins 31b at opposite ends, are axially movably inserted within guide holes 30a, which are inner diametric holes of the respective guide pipes 30. One of the pillar shaped pins 31b, which is on the side of the distal end member 2, has its tip representing a spherical shape and is held in contact with a base end face of the distal end member housing 11. The base end face 11b of the housing 11, which defines a surface of contact between the distal end member 2 and the attitude altering member 31, for the distal end member 2 is so shaped as to represent an inclined face such that an outer peripheral edge thereof is closer to the spindle guide section 3 than a center portion thereof. Similarly, the other of the pillar shaped pins 31b, that is, the pillar shaped pin 31b on the side of the main body housing 4 has its tip representing a spherical shape and held in contact with a side face of a lever 43 (FIG. 14A) as will be described in detail later.

It is to be noted that the use of the pillar shaped pins 31b may be dispensed with, leaving only the signal wire 31a to constitute the attitude altering member 31.

Also, three reinforcement shafts 34 are arranged between the inner diametric surface of the outer shell pipe 25 and the drive transmitting unit 22 and on the pitch circle C of the same diameter as the guide pipe 30 in a fashion alternating with the guide pipes 30. Those reinforcement shafts 34 are used to secure the rigidity of the spindle guide main body 3a. The guide pipe 30 and the reinforcement shafts 34 are arranged equidistantly relative to each other around the drive transmitting unit 22. The guide pipe 30 and the reinforcement shafts 34 are held in contact with the inner diametric surface of the outer shell pipe 25 and respective outer peripheral surfaces of the rolling bearings 26. In this manner, the outer diametric surfaces of those rolling bearings 26 are supported.

FIGS. 14A and 14B illustrate the tool rotation drive mechanism 4b and the attitude altering drive mechanism 4c within the main body housing 4. The tool rotation drive mechanism 4b includes a tool rotation drive source 41. The tool rotation drive source 41 is employed in the form of, for example, an electrically operated motor, an output shaft 41a of which is connected with the base end of a rotary shaft or the drive transmitting unit 22. It is to be noted that the rotary shaft 22 is passed through an opening 44 defined in a lever 43bU as will be described later.

The attitude altering drive mechanism 41 includes three attitude altering drive sources 42 (42U, 42L and 42R) each employed for the associated attitude altering member 31 (31U, 31L and 31R). This attitude altering drive source 42 is in the form of, for example, an electrically operated linear actuator and had an output rod 42a capable of moving leftwards or rightwards, as viewed in FIG. 14A, the movement of such output rod 42a being transmitted to the attitude altering member 31 through a lever mechanism 43, which is a force transmitting mechanism. The amount of actuation of the attitude altering drive source 42 is detected by a tool attitude detector 45. A detection signal outputted from this tool attitude detector 45 is supplied to an estimating unit 85 (best shown in FIG. 15) of the navigation computer 9 through an actuator electric cable 52 (best shown in FIG. 12).

The lever mechanism 43 includes a pivot lever 43b (43bU, 43bL, 43bR) pivotable about a support pin 43a and is so designed and so configured as to allow a force of the output rod 42a to work on a working point P1 of the lever 43b, which is spaced a long distance from the support pin 43a, and as to apply a force to the attitude altering member 31 at a force point P2, which is spaced a short distance from the support axis 43a, wherefore an output of the attitude altering drive source 42 can be increased and then transmitted to the attitude altering member 31. Since the use of the lever mechanism 43 is effective to enable a large force to be applied to the attitude altering member 31 even in the linear actuator of a low output capability, the linear actuator can be downsized. It is to be noted that instead of the use of the attitude altering drive source 42 or the like, the attitude of the distal end member 2 may be manually operated from a remote site by remote control.

As shown in FIG. 15, the operating system unit 5b is made up of a tool rotation controller 5ba and an attitude controller 5bb. The operating system unit 5b is comprised of hardware and a software program executed thereby, or comprised of a further addition of an electronic circuit. The tool rotation controller 5ba provides an output to a motor driver (not shown) in response to an input from a rotation operating instrument 51a so as to drive the tool rotation drive source 41. The attitude controller 52b provides an output to the motor driver (not shown) in response to an input from an attitude altering instrument 1b to thereby drive the attitude altering drive source 42.

Referring still to FIG. 15, as hereinbefore described, the navigation system includes the tool tip position detecting device 53 and the display device 80. Also, the tool tip position detecting device 53 in turn includes the external force free position detector 54, the strain detectors 62X and 62Y, and the corrector 55. The display device 80 in turn includes the display unit 56 for the computer 9, an actuator display information generator 86 and an object display information generator 87.

The external force free position detector 54 in turn includes a maker detecting machine 8 operable to detect the position and the attitude of an actuator marker 7A fitted to the remote controlled actuator 5. This marker detecting unit 8 corresponds to the detecting machine 54a of a kind hereinbefore described in connection with the previously described embodiment. Also, the marker detecting unit 8 employed in the practice of this embodiment is also operable to detect the position and the attitude of an object marker 7B fitted to the object 6 to be processed.

As shown in FIG. 12, the marker detecting unit 8 includes individual detectors 8b supported by a detector support body 8a and marker position and attitude calculators 84A and 84B within the computer 9 (FIG. 15). The actuator marker 7A is fitted to the main body housing 4, which forms a part of the actuator main body 10. The to-be-processed object marker 7B is fitted to the object to be processed 6 such as, for example, a bone. In correspondence with the individual detectors 8b of the marker detecting unit 8, each of the markers 7A and 7B is provided with three light reflectors 7a. Those three light reflectors 7a are disposed at different positions, respectively.

Each of the marker detectors 8b is of an optical type and is so designed and so configured as to project a detection beams towards the light reflectors 7a of each of the markers 7A and 7B and then receive rays of light reflected from those light reflectors 7a. Respective detection signals of those marker detectors 8b are supplied to respective marker position and attitude calculators 84A and 84B (FIG. 15) in the computer 9 through a wiring system (not shown), built in the detector support body 8a, and a marker detector electric cables 81. It is, however, to be noted that the use of three light projectors (not shown) may be provided respectively in the markers 7A and 7B so that detection beams projected from those light projectors can be received by the individual detectors 8b. The use of the marker detectors 8b of an optical type as discussed above is effective to allow the marker detecting unit 8 to be assembled portable. It is, however, also to be noted that each of the marker detectors 8b may not necessarily be of an optical type and may be of, for example, a magnetic type.

As shown in FIG. 15, the computer 9 includes a navigation system unit 82 and the display unit 56. The navigation system unit 82 is comprised of hardware of the computer 9 and a software program executed thereby, or comprised of a further addition of an electronic circuit.

The navigation system unit 82 includes, as structural elements of the external force free position detector 54 within the tool tip position detecting device 53, a relative position storage unit 83, the marker position and attitude calculators 84A and 84B and an estimating unit 85. The relative position storage unit 83 in turn includes a spindle guide main body type selector 83a and a tool type selector 83b. The relative position storage unit 83, the marker position and attitude calculators 84A and 84B and the estimating unit 85 correspond to the storing and calculating section 54b of the external force free position detector 54. Also, as structural elements other than the external force free position detector 54 within the tool tip position detecting device 53, the navigation system unit 82 includes the strain detectors 62X and 62Y and the corrector 55. Furthermore, as structural elements of the display device 80, the navigation system unit 82 includes the actuator display information generator 86 and the object display information generator 87. The display information generators 86 and 87 correspond to the display information generator 57 employed in the practice of the previously described embodiment.

The relative position storage unit 83 is operable to store therein information on the relative position of the pivot center O1 of the distal end member 2 relative to the actuator marker 7A fitted to the main body housing 4 and information on the shape of the tool 1 with reference to the pivot center O1. For the information on the shape of the tool 1, information can be employed, which pertains to the relative position of the center O2 (FIG. 13A) of the processing member 1a relative to the pivot center O1 when the attitude of the distal member 2 held at, for example, a neutral position. This information on the relative position may be merely the distance between the pivot center O1 of the distal end member 2 and the center O2 of the processing member 1a.

The relative position storage unit 83 will be described in further details hereinafter.

Figure 16A:
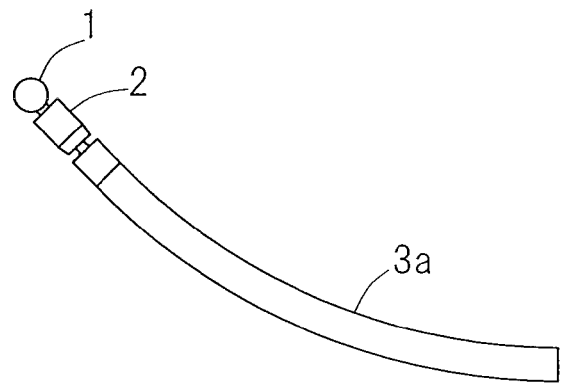
FIG. 16A is a side view showing a tool and the spindle guide of the remote controlled actuator.
Figure 16B:
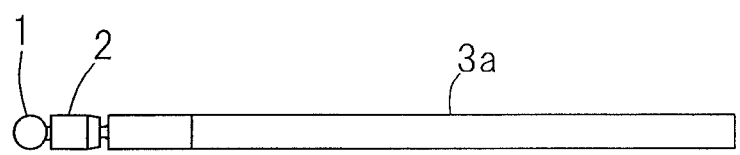
FIG. 16B is side view showing the tool and the spindle guide of a different shape.
Figure 17:
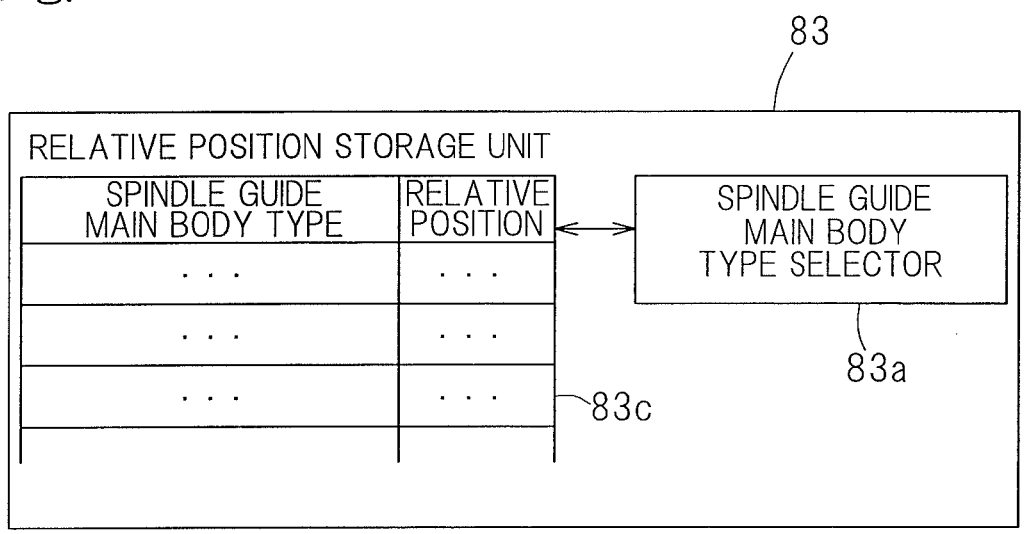
FIG. 17 is a diagram showing a structure of a portion of a relative position storage unit of the navigation system.

The relative position of the pivot center O1 of the distal end member 2 relative to the actuator marker 7A depends on the shape of the spindle guide main body 3a. By way of example, depending on whether the spindle guide main body 3a used is of a curved configuration as best shown in FIG. 16A or whether the spindle guide section 3 is of a linear configuration as best shown in FIG. 16B, the relative position referred to above differs. Even when the spindle guide main body 3a is deformed, for example, artificially, the relative position referred to above differs before and after the deformation. As shown in FIG. 17, the relative position storage unit 83 accommodates therein a table 83c recording and storing relations between the types of the spindle guide main body 3a and the relative positions, and from those plural relations stored and preserved in this table 83c, the spindle guide main body type selector 83a selects a proper one of those relations in dependence on information inputted from outside. The relative positions of the spindle guide main body 3a for each of those types is determined in reference to design data measured beforehand.

Figure 18A:
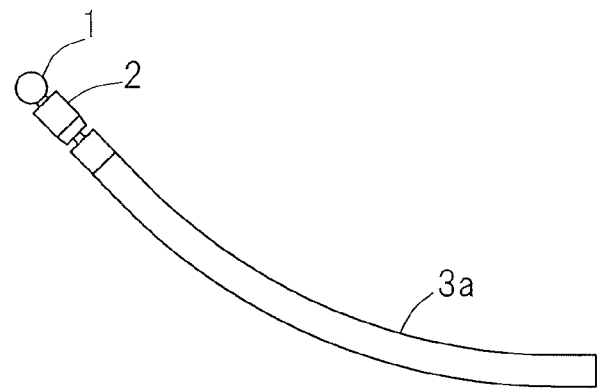
FIG. 18A is a side view showing the tool and the spindle guide of the remote controlled actuator.
Figure 18B:
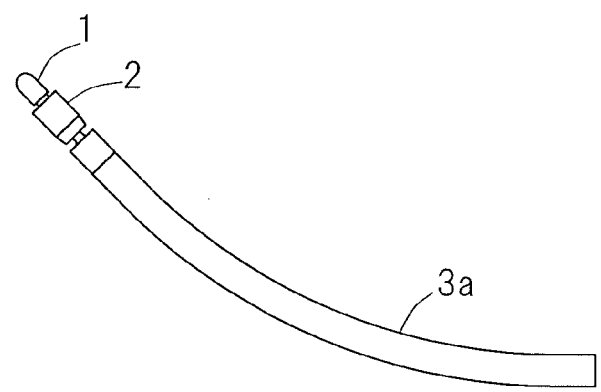
FIG. 18B is a side view showing a different type of the tool and the spindle guide.
Figure 19:
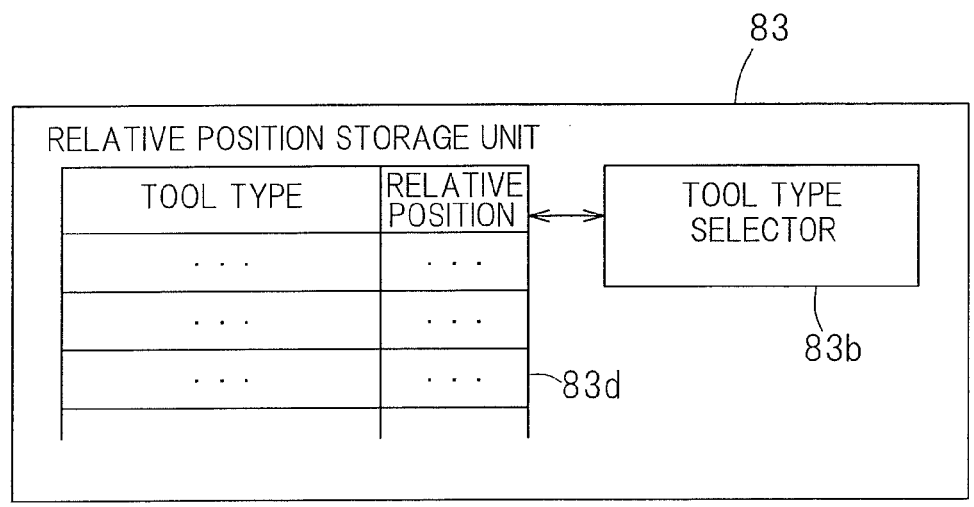
FIG. 19 is a diagram showing a structure of a portion of the relative position storage unit of the navigation system.

Also, the shape of the tool 1 with reference to the pivot center O1 differs depending on the type of the tool 1 used. By way of example, depending on whether the tool 1 is employed in the form of the type having the spherical processing member 1a as best shown in FIG. 18A or whether the tool 1 is employed in the form of the type having a pillar shaped configuration as best shown in FIG. 18B, the relative position referred to above differs. As shown in FIG. 19, the relative position storage unit 83 accommodates therein a table 83d storing and preserving relations between the types of the tools 1 and the relative positions, and from those plural relations stored and preserved in this table 83d, the tool type selector 83b selects a proper one of the relations in dependence on information inputted from outside. The relative position of the tool 1 for each of those types is determined in reference to design data or measurements beforehand. Information concerning the shape of the tool 1 may be employed, for example, in the form of information on the relative position of a processing end Q (FIG. 13A) of the processing member 1a relative to the pivot center O1 when the attitude of the distal end member 2 is in the neutral position. The processing end Q referred to above is a tip end of the tool 1 lying on a rotational center line (the center line of the spindle 13) CL and is a site that is mainly held in contact with the to-be-processed object 6.

The marker position and attitude calculator 84A is operable to calculate the position and the attitude of the actuator marker 7A, fitted to the main body housing 4, from detection signals of the individual detectors 8b of the marker detecting unit 8. With the light reflectors 7a of the marker 7A as well as the individual detectors 8b of the marker detecting unit 8 being employed in three or more in number, the three dimensional position and attitude of the marker 7A can be determined. The position and the attitude of the actuator marker 7A are analogous to the position and the attitude of the actuator main body 10. In other words, by the marker position and attitude calculator 84A, the position and attitude of a reference portion of the actuator main body 10 is detected. The term "reference portion" referred to above and hereinafter is intended to mean a portion that provides a basis for calculation performed by the estimating unit 85 as will be described later.

Similarly, the marker position and attitude calculator 84B is operable to calculate the position and the attitude of the to-be-processed object marker 7B, fitted to the to-be-processed object 6, from the detection signals of the individual detectors 8b of the marker detecting unit 8. The position and attitude of the to-be-processed object marker 7B is analogous to the position and the attitude of the to-be-processed object 6.

The estimating unit 85 is operable to estimate the position of the processing member 1a of the tool 1, that is, the tip position of the tool 1 from the information on the position and attitude of the actuator marker 7A which has been determined by the marker position and attitude calculator 54A, the information on the relative position of the pivot center O1 of the distal end member 2 relative to the actuator marker 7A selected by the relative position storage unit 83, the information on the shape of the tool 1 with the pivot center O1 taken as a reference selected by the relative position storage unit 83, and the information on the attitude of the distal end member 2 detected by the tool attitude detector 45.

In other words, the estimating unit 85 can estimate the absolute position of the pivot center O1 from the information on the position and attitude of the actuator marker 7A detected by the marker detecting unit 8, that is, the position and attitude of the reference portion of the actuator main body 10, and the information on the relative position of the pivot center O1 of the distal end member 2 relative to the marker 7A stored in the relative position storage unit 83. Also, the relative position of the processing member 1a of the tool 1 relative to the pivot center O1 can be estimated from the information on the attitude of the distal end member 2 relative to the actuator main body 10, detected by the tool attitude detector 45, and the information on the shape of the tool 1 stored in the relative position storage unit 83.

From the absolute position of the center of pivot O1 of the distal end member 2 and the relative position of the processing member 1a with the pivot center O1 taken as a reference, so estimated in the manner described above, the absolute position of the processing member 1a of the tool 1 can be estimated. For this reason, relative to the remote controlled actuator 5 capable of altering, by remote control, the attitude of the distal end member 2 for the support of the tool 1, which is provided at the distal end of the spindle guide main body 3a, the position of the processing member 1a of the tool 1 can be estimated.

The strain detectors 62X and 62Y are operable to detect strains occurring in X-axis and Y-axis directions, respectively, of the spindle guide 3, each comprised of a bridge circuit including a combination of the pair of the strain sensors 60 (FIG. 2) which are provided at the base end of the spindle guide 3, and the two resistors 61 (FIG. 2), in a manner similar to that in the previously described embodiment. Also, the corrector 55 corrects the tip position of the tool 1, detected by the external force free position detector 54, with the use of the respective detected strain values of the strain detectors 62X and 62Y in a manner similar to that in the previously described embodiment. Accordingly, a displacement of the tip position of the tool 1 resulting from flexure of the spindle guide 3 is corrected and the accurate tip position of the tool 1 can be detected.

The actuator display information generator 86 is operable to calculate an actuator display information, which is information for displaying the position and attitude of the actuator main body 10, the shape of the spindle guide main body 3a and the attitude of the distal end member 2 from various pieces of information used to estimate the position of the tool 1 by means of the estimating unit 85 and the information on the accurate tip position of the tool 1 which has been corrected by the corrector 55, and then to display a result of such calculation on a screen of the display unit 56. Also, the object display information generator 87 is operable to calculate an object display information, which is information on the position and attitude of the object marker 7B determined by the marker position and attitude calculator 84B and then to display a result of such calculation on the screen of the display unit 56.

Figure 20:
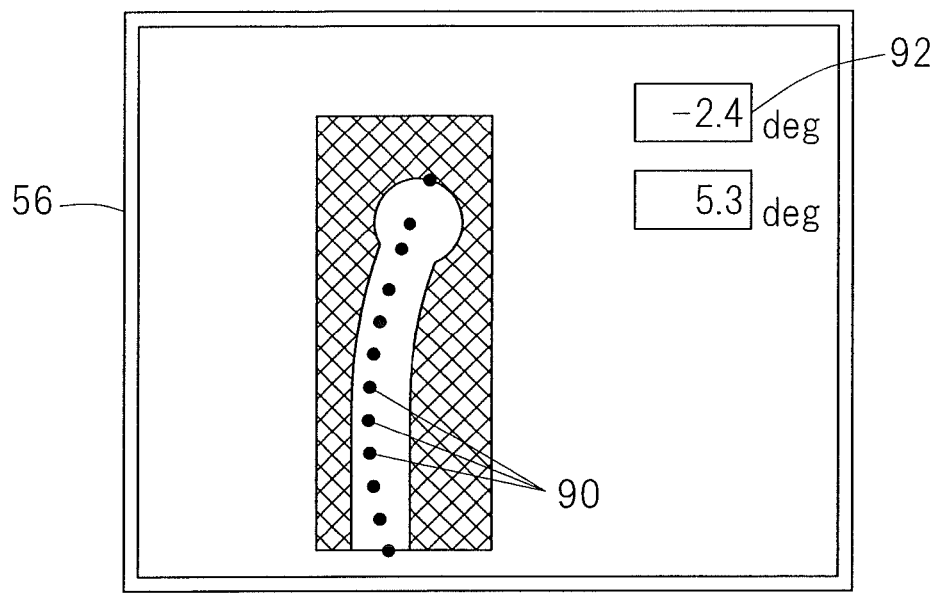
FIG. 20 is a diagram showing an example of screen display appearing in a display unit employed in the navigation system.
Figure 21:
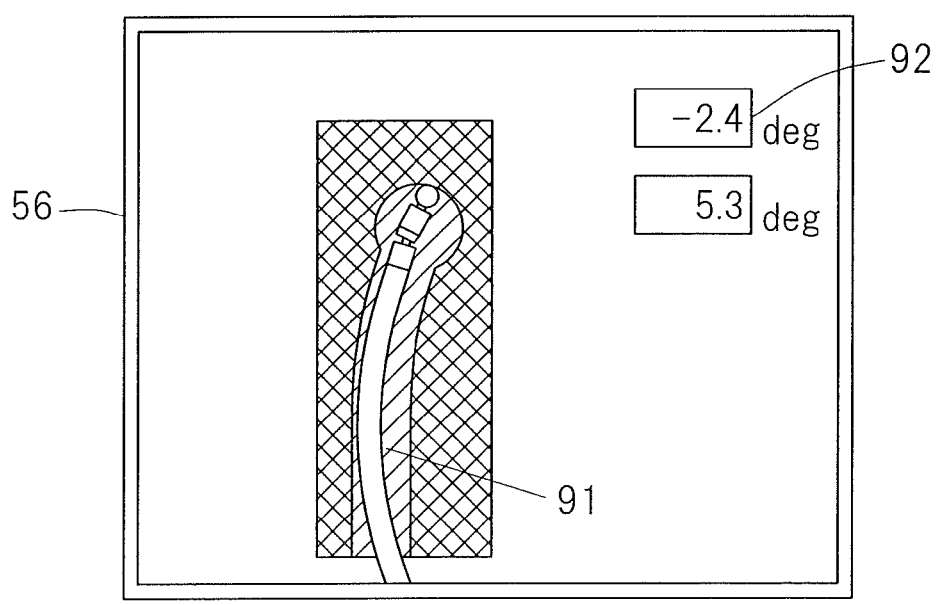
FIG. 21 is a diagram showing a different example of screen display appearing in a display unit employed in the navigation system.
Figure 23A:
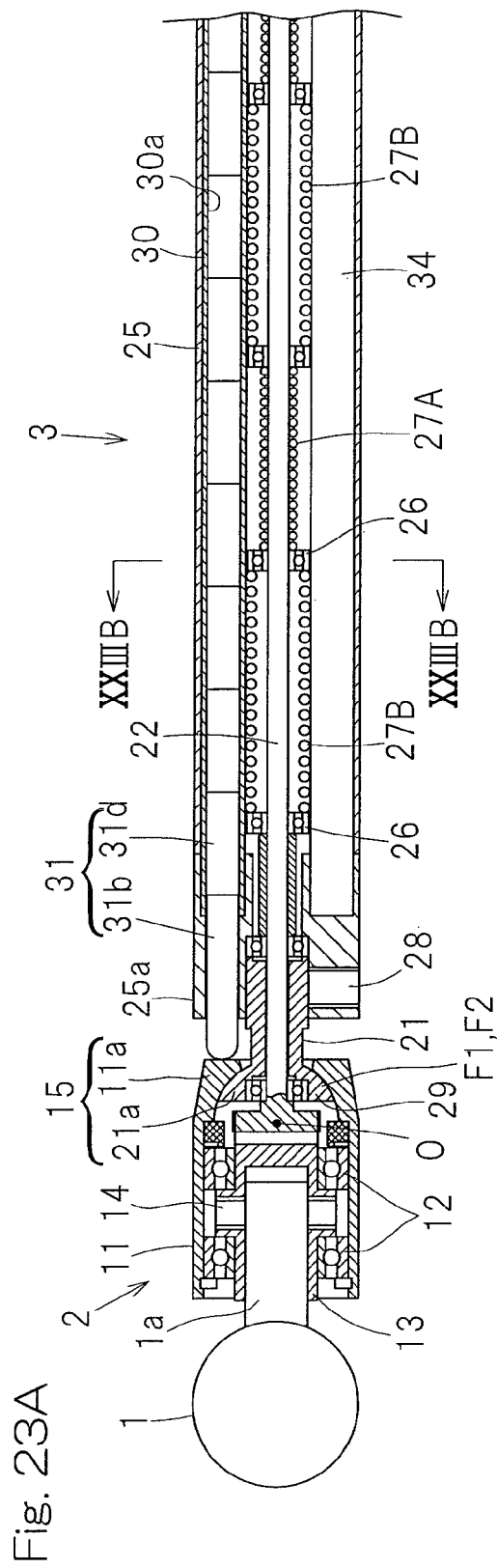
FIG. 23A is a longitudinal sectional view showing the tool and the spindle guide of the remote controlled actuator according to a fifth preferred embodiment of the present invention.
Figure 23B:
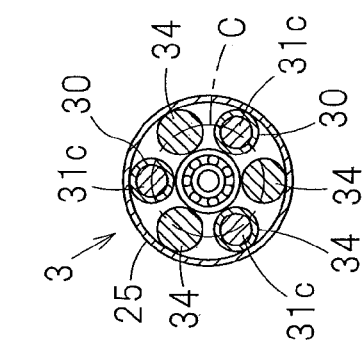
FIG. 23B is a cross sectional view taken along the line XXIIIB-XXIIIB in FIG. 23A.

More specifically, as best shown in FIG. 20, the actuator display information and the object display information, both referred to above, that is, the position and attitude of the actuator main body 10, the shape of the spindle guide main body 3a, the attitude of the distal end member 2 and the position and attitude of the to-be-processed object 6 are displayed in the form of a plurality of dots 90. FIG. 20 illustrates respective positions of the spindle guide main body 3a and the distal end member 2 being displayed in the form of the dots 90 spaced a predetermined distance from each other. Alternatively, as best shown in FIG. 21, using a computer graphics, a representation 91 is displayed, which represents respective contours of the position and attitude of the actuator main body 10, the distal end member 2, the tool 1 and the to-be-processed object 6. Yet, the actuator display information and the object display information may be displayed on display windows 92 in terms of numerical representations together with the dots 90 and the graphic symbol 91 as shown in FIGS. 20 and 21. In the illustrated example, there is illustrated a condition in which the attitude of the distal end member 2 is displayed on the display windows 92. It is preferred that information other than the attitude of the distal end member 2 can also be selectively displayed.

Hereinafter, the operation of the remote controlled actuator 5 will now be described.

When the tool rotation drive source 41 is driven, the rotational force thereof is transmitted to the spindle 13 through the drive transmitting unit 22, resulting in rotation of the tool 1 together with the spindle 13. By the tool 1 thus driven, cutting of the bone or the like is performed. The rotational speed of the tool 1 can be set to an arbitrary value by means of the rotation operating instrument 51a.

When in use, by driving the three attitude altering drive sources 42 (42U, 42L and 42R) and selectively advancing or retracting the attitude altering members 31 (31U, 31L and 31R) in association therewith, the attitude of the distal end member 2 is altered by remote control. This attitude altering operation is carried out by means of the attitude altering instrument 51b.

By way of example, when one of the attitude altering members 31U, which is shown in an upper side of FIG. 13A, is advanced towards the tip end side while the other two attitude altering members 31L and 31R are retracted, the housing 11 for the distal end member 2 is pressed by the attitude altering member 31U shown in the upper side of FIGS. 13A and 13B to allow the distal end member 2 to be altered in attitude along the guide surfaces F1 and F2 with the tip end side consequently oriented downwardly as viewed in FIG. 13A. At this time, those attitude altering drive sources 42 are controlled so that the amount of advance or retraction of each of the attitude altering members 31 may become proper. On the other hand, when each of those attitude altering members 31 is conversely retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 13A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 13A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased.

Since the attitude altering member 31 is inserted through the guide hole 30a, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is comprised of mainly the wire 31a and has a flexible property, the attitude altering operation of the distal end member 2 is carried out accurately even though the spindle guide main body 3a is curved. In addition, since the center of the junction between the spindle 13 and the drive transmitting unit 22 lies at the same position as the respective centers of curvature O1 of the guide faces F1 and F2, no force tending to press and pull will not act on the drive transmitting unit 22 as a result of the alteration of the attitude of the distal end member 2 and the distal end member 2 can be smoothly altered in attitude.

The remote controlled actuator 5 of the foregoing construction is utilized in grinding the femoral marrow cavity during, for example, the artificial joint replacement surgery and during the surgery, it is used with the distal end member 2 in its entirety or a part thereof inserted into the body of a patient. Because of this, if the distal end member 2 can be altered in attitude by remote control, the bone can be processed in a condition with the tool 1 maintained in a proper attitude at all times and the opening for insertion of the artificial joint can be finished accurately and precisely.

There is the necessity that the drive transmitting unit 22 and the attitude altering member 31 are provided in a protected fashion. In this respect, the spindle guide main body 3a, which is elongated in shape, is provided with the drive transmitting unit 22 at the center of the outer shell pipe 25 and the guide pipe 30, accommodating therein the attitude altering member 31, and the reinforcement shafts 34, all of these are arranged in the circumferential direction and between the outer shell pipe 25 and the drive transmitting unit 22. Accordingly, the drive transmitting unit 22 and the attitude altering member 31 can be protected and the interior can be made hollow to thereby reduce the weight without sacrificing the rigidity. Also, the arrangement balance as a whole is rendered good.

Since the outer diametric surfaces of the rolling bearings 26 supporting the drive transmitting unit 22 are supported by the guide pipe 30 and the reinforcement shafts 34, the outer diametric surfaces of the rolling bearings 26 can be supported with no need to use any extra member. Also, since the preload is applied to the rolling bearings 26 by means of the spring elements 27A and 27B, the drive transmitting unit 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide main body 3a.

During the operation of the remote controlled actuator 5, the respective positions of the tool 1 and the to-be-processed object 6 are detected by the navigation system and are then displayed on the screen of the display unit 56. Because of this, even when the tool 1 is not visible directly with eyes because the tool 1 is then positioned inside the to-be-processed object 6 such as, for example, the bone, the operator can manipulate the tool 1 while looking at the screen of the display unit 56 to ascertain the position of the tool 1 and the position of the to-be-processed object 6. Also, where the respective positions and attitudes of the actuator main body 10, the distal end member 2, the tool 1 and the to-be-processed object 6 are displayed in the form of the plural dots 90 or the contours thereof are displayed in the form of the graphic symbol 91, the position of the tool 1 relative to the to-be-processed object 6 can readily be grasped visually.

In the event that the spindle guide main body 3a is replaced with a different type and/or the shape of the spindle guide main body 3a is deformed, it can be accommodated as the proper relation can be selected by the spindle guide main body type selector 83a out from the relations between the types of the spindle guide main bodies 3a and the relative position of the distal end member 2, which are stored in the table 83c of the relative position storage unit 83. Similarly, even in the event that the tool is replaced with a tool of a different shape, it can be accommodated as the proper relation can be selected by the tool type selector 83b from the relations between the types of the tools 1 and the relative position of the processing member 1a, which are stored in the table 83d of the relative position storage unit 83.

The attitude altering member 31 may be comprised of a plurality of force transmitting members 31c and 31d that are arranged gapless in a direction conforming to the lengthwise direction of the guide hole 30a such as employed in the practice of fourth and fifth preferred embodiments of the present invention shown in FIGS. 22A and 22B and FIGS. 23A and 23B, respectively. In the fourth embodiment shown in FIGS. 22A and 22B, the plural force transmitting members 31c are in the form of balls and a pillar shaped pin 31b is provided on a tip side of arrangement of those balls. In the fifth embodiment shown in FIGS. 23A and 23B, the plural force transmitting members 31d are in the form of cylindrical pillar-like elements and a pillar shaped pin 31b is provided on a tip side of arrangement of those pillar shaped elements. The pillar shaped pin 31b is the one similar to that described previously and is held in contact with the base end face 11b of the housing 11. Even in this case, the attitude altering member 31, without displacing in a direction perpendicular to the lengthwise direction thereof, properly acts on the distal end member 2 at all times and, therefore, the attitude altering operation of the distal end member 2 takes place accurately. Also, the attitude altering member 31 in its entirety is of a structure having a flexible property and, hence, even in a condition in which the spindle guide section 3 is curved, the attitude altering operation of the distal end member 2 takes place assuredly.

In the construction shown in and described with reference to each of FIGS. 13A to 13C, FIGS. 22A and 22B and FIGS. 23A and 23B, where the guide section 3 is allowed to assume a curved shape, it is necessary for the outer shell pipe 25, the guide pipe 30 and the reinforcement shaft 34 to be curved. Also, it is preferred that the drive transmitting unit 22 makes use of an easily deformable material and a shape memory alloy, for example, is suited.

Figure 24:
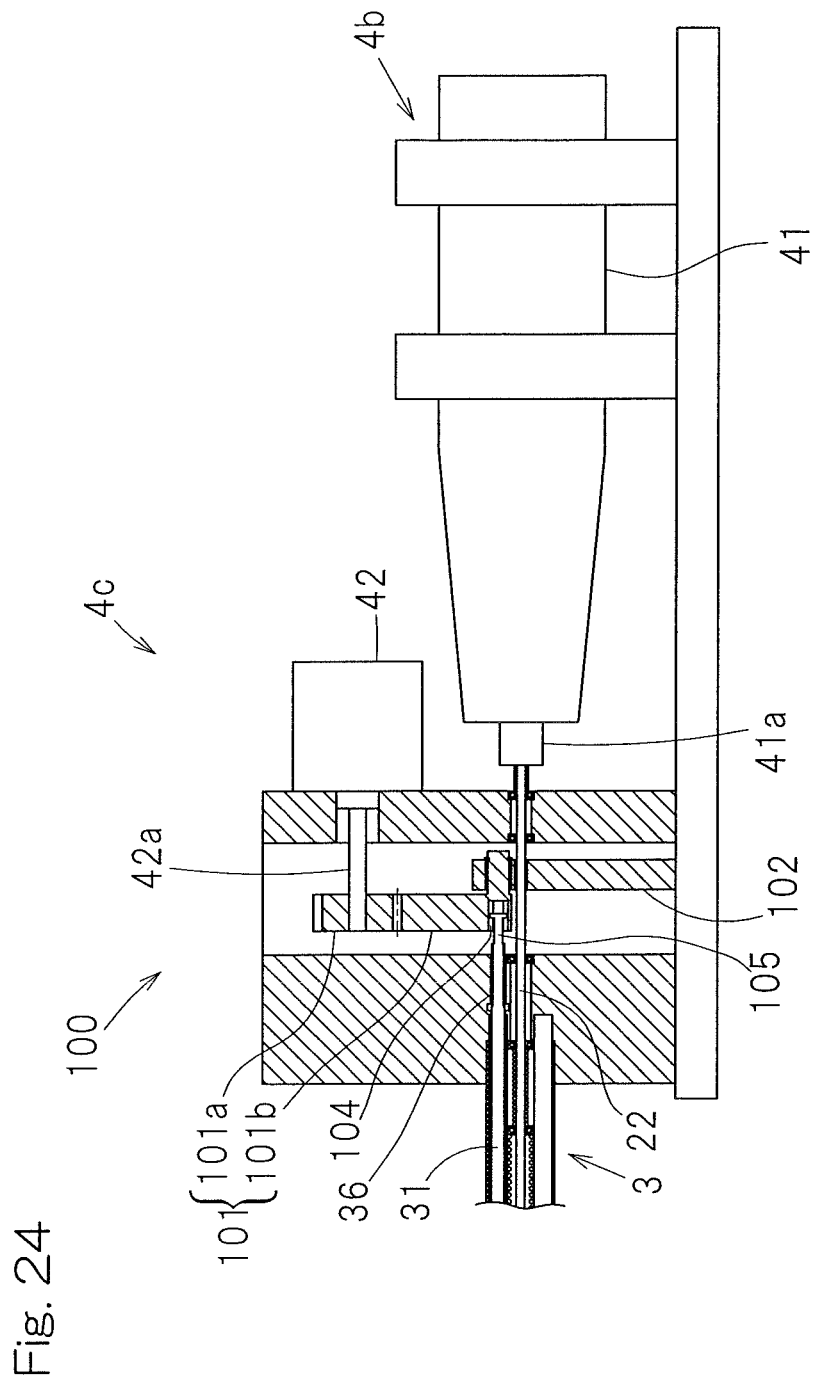
FIG. 24 is a side view showing, with a portion cut out, the tool rotation drive mechanism and the attitude altering drive mechanism for the remote controlled actuator according to a sixth preferred embodiment of the present invention, which makes use of a attitude altering drive mechanism of a different construction.
Figure 25B:
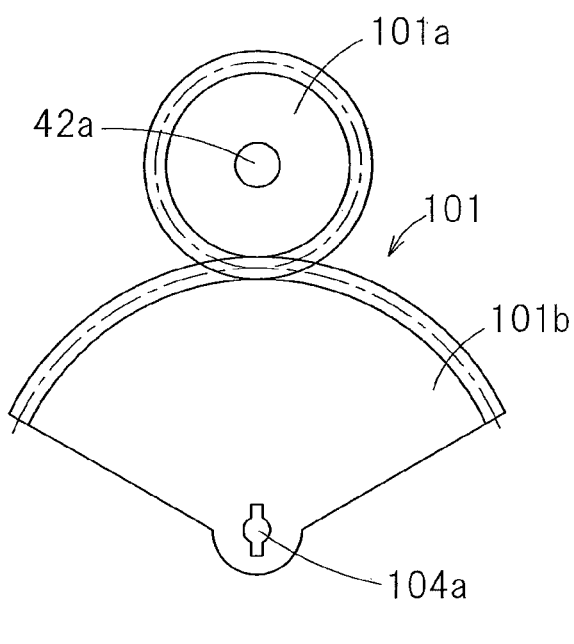
FIG. 25B is a side view of FIG. 25A.
Figure 25A:
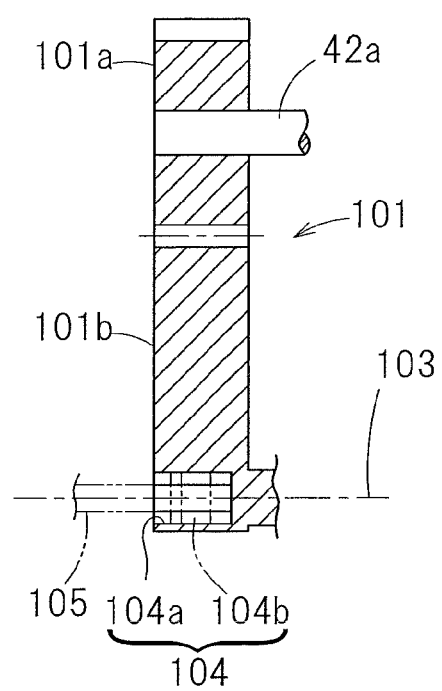
FIG. 25A is a front elevational view showing a reduced speed rotation transmitting mechanism for the remote controlled actuator.
Figure 26:
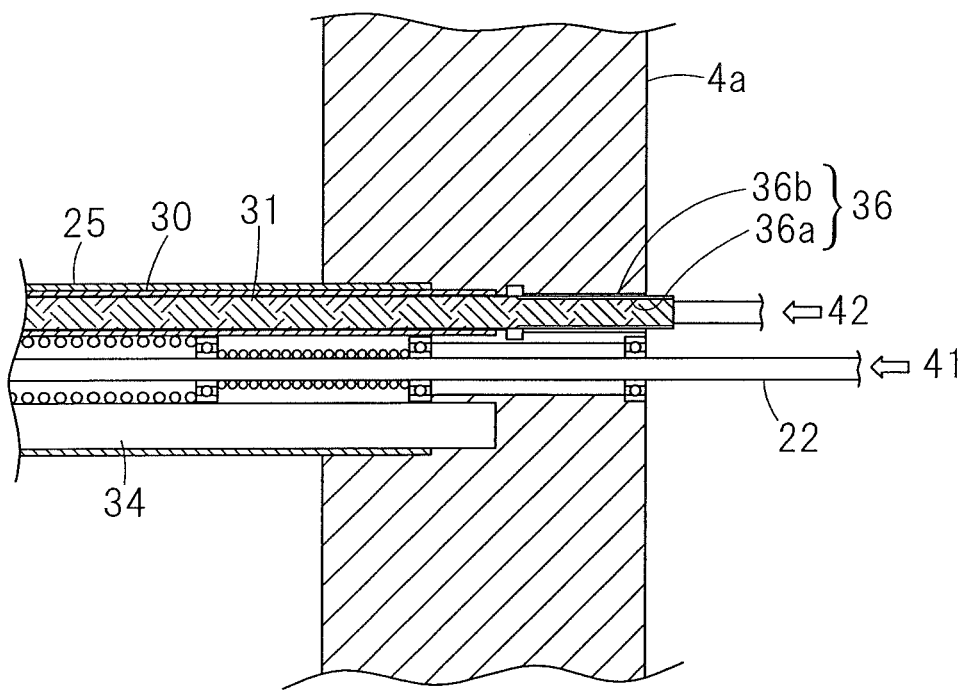
FIG. 26 is a diagram showing, on an enlarged scale, a connection between an attitude altering member and a main body housing of the remote controlled actuator.

The attitude altering drive mechanism may be of such a construction as in a sixth preferred embodiment of the present invention shown in FIGS. 24 to 26. This attitude altering drive mechanism 4c is comprised of an attitude altering drive source 42 and a drive mechanism section 100 for transmitting an operation of the attitude altering drive source 42 to the attitude altering member 31. The attitude altering drive source 42 is in the form of, for example, an electrically operated rotary actuator. The drive mechanism section 100 is made up of a speed reducing and rotation transmitting mechanism 101 and a screw mechanism 36.

As shown in FIGS. 25A and 25B, the speed reducing and rotation transmitting mechanism 101 includes a round spur gear 101a, fitted to an output shaft 42a of the attitude altering drive source 42, and a sector shaped spur gear 101b rotatably supported by a support member 102 (FIG. 24) fixed to the main body housing 4 and meshed with the round spur gear 101a and is so designed that by means of a rotary slide portion 104 provided on a center axis 103 of rotation of the sector shaped spur gear 101b, the rotation can be transmitted from the sector shaped spur gear 101b to a base end side extension 105 of the attitude altering member 31. The rotary slide portion 104 is made up of a grooved hole 104a, formed in the sector shaped spur gear 101b, and a projection equipped shaft 104b of the base end side extension 105, and the projection equipped shaft 104b is axially movably, but not rotatably engaged in the grooved hole 104a. Since the pitch circle diameter of the sector shaped spur gear 101b is greater than that of the round spur gear 101a, the rotation of the output shaft 42a is reduced in speed and is then transmitted to a base end of the wire 31, which is the attitude altering member.

As best shown in FIG. 26, the screw mechanism 36 is made up of a male screw portion 36a, formed in the base end of the attitude altering member 31 in the form of the wire, and a female screw portion 36b formed in the main body housing 4 and meshed with the male screw portion 36a. When the base end of the attitude altering member 31 is rotated by the drive of the attitude altering drive source 42 (FIG. 24), the attitude altering member 31 is selectively advanced or retracted by the action of the screw mechanism 36. When the attitude altering member 31 is advanced or retracted by the action of the screw mechanism 36 in this way, in the event of the external force being applied to the tool 1 or the distal end member 2, an axially acting force is applied from the distal end member 2 to the attitude altering member 31. However, since the structure is employed in which the attitude altering member 31 is advanced or retracted by the screw mechanism 36, the attitude altering member 31, unless rotated in a direction of rotation, will not move axially. For this reason, the attitude stability of the distal end member 2 against the external force is good.

Since the speed reducing and rotation transmitting mechanism 101 is provided, the base end of the attitude altering member 31 in the form of the wire can be rotated at a low speed even with a compact rotary actuator in which the attitude altering drive source 42 rotates at a high speed. For this reason, it becomes possible to employ a compact rotary actuator for the attitude altering drive source 42. Also, since the rotary actuator is employed for the attitude altering drive source 42, it is sufficient to transmit the rotational output of this rotary actuator directly to the base end of the attitude altering member 31 in the form of the wire and the drive mechanism section 100 can therefore be simplified. It is to be noted that the tool rotation drive mechanism 4b is of a structure similar to that described hereinbefore.

FIGS. 27 to 30 illustrate a seventh preferred embodiment of the present invention which makes use of the tool rotation drive mechanism and the attitude altering drive mechanism, both having respective structures different from those described hereinbefore. While in the previously described embodiment or embodiments, the tool rotation drive source 41 of the tool rotation drive mechanism 4b and the attitude altering drive source 42 of the attitude altering drive mechanism 4c are provided within a drive unit housing 4a, the tool rotation drive source 41 and the attitude altering drive source 42 both employed in the practice of the seventh embodiment are provided within a drive source housing 110 that is separate from the drive unit housing 4a.

Figure 29:
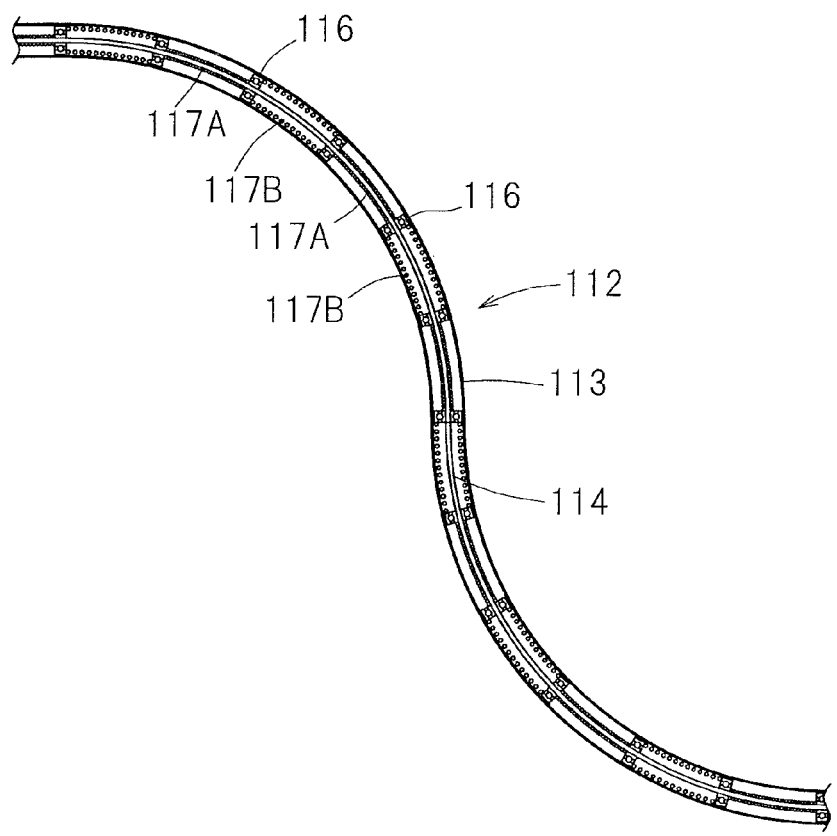
FIG. 29 is a longitudinal sectional view showing a tool rotation cable employed in the tool rotation drive mechanism.

The tool rotation drive mechanism, now identified by 111, employed in the seventh embodiment is of such a structure that the rotation of the output shaft 41a of the tool rotation drive source 41 provided within the drive source housing 110 can be transmitted to the base end of the drive transmitting unit 22 within the drive unit housing 4a by means of an inner wire 114 (best shown in FIG. 29) of a tool rotation cable 112. The tool rotation cable 112 is, for example, of such a structure as shown in FIG. 29. Specifically, the flexible inner wire 114 is rotatably supported by a plurality of rolling bearings 116 at a center of a flexible outer tube 113. Opposite ends of the inner wire 114 is connected respectively with a base end of the output shaft 41a of the tool rotation drive source 41 and a base end of the drive transmitting unit 22. Between the neighboring rolling bearings 116, spring elements 117A and 117B are provided for generating a preload to those rolling bearings 116. The spring elements 117A and 117B are in the form of, for example, compression coil springs. There are the spring element 117A for an inner ring to generate a preload to the inner ring of the rolling bearing 116 and the spring element 117B for an outer ring to generate a preload to the outer ring, and those are arranged alternately. With the preloads applied to the rolling bearings 116 through the spring elements 117A and 117B in this way, the inner wire 114 can be rotated at a high speed. It is to be noted that a commercially available flexible shaft may be employed for the tool rotation cable 112.

Also, the attitude altering drive mechanism 121 employed in the practice of the seventh embodiment is of such a structure that the rotation of the output shaft 42a of the attitude altering drive source 42 provided within the drive source housing 110 can be transmitted to the drive mechanism section 100 within the drive unit housing 4a through an attitude alteration cable 122. The drive mechanism section 100 is of a structure similar to that shown in and described with particular reference to FIGS. 24 to 26 and, therefore, component parts similar to those shown are designated by like reference numerals. The round spur gear 101a of the speed reducing and rotation transmitting mechanism 101 is fitted to a gear mounting shaft 125 that is rotatably supported by the drive unit housing 4a through rolling bearings 125a. The attitude altering drive source 42 is employed in the form of a rotary actuator and the rotation of the attitude altering drive source 42 is transmitted to the gear mounting shaft 125 through the inner wire 124 (best shown in FIG. 30) of the attitude alteration cable 122.

Figure 30:
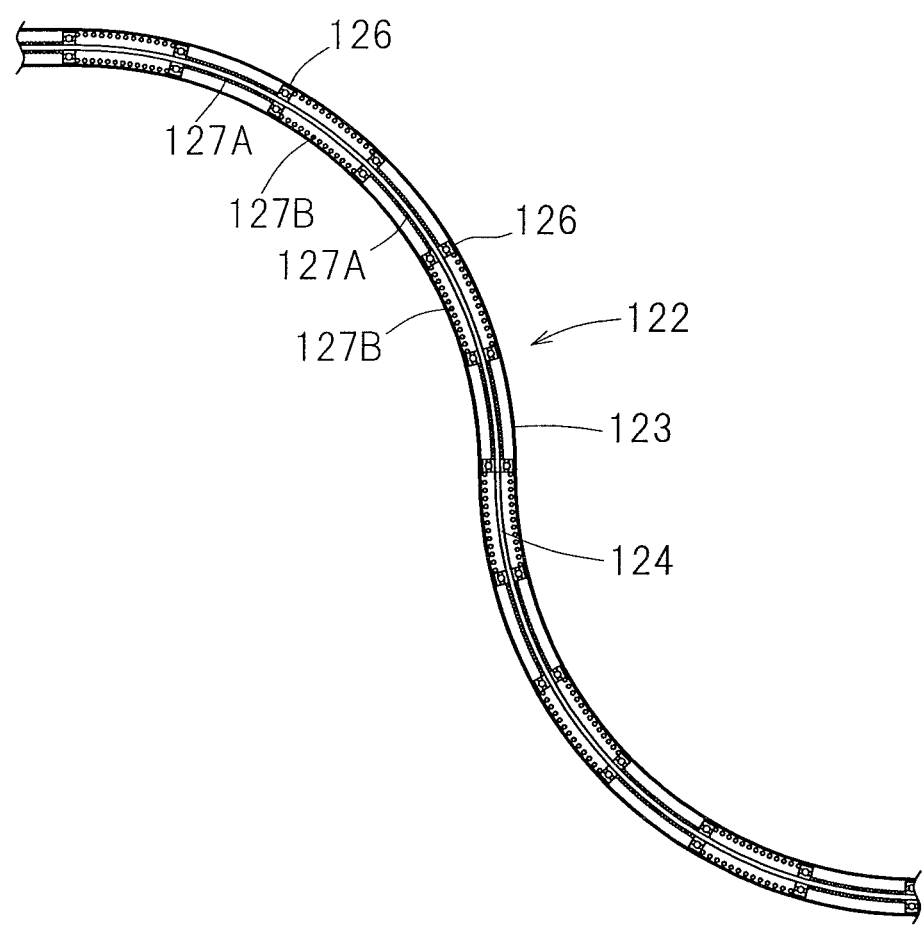
FIG. 30 is a longitudinal sectional view showing an attitude alteration cable employed in the attitude altering drive mechanism.

The attitude alteration cable 122 is of a structure similar to that of the previously described tool rotation cable 112 and has, for example, such a structure as shown in FIG. 30. Specifically, a flexible inner wire 124 is rotatably supported by a plurality of rolling bearings 126 at the center of a flexible outer tube 123. Opposite ends of the inner wire 124 is connected respectively with a base end of the output shaft 42a of the attitude altering drive source 42 and a base end of the gear mounting shaft 125. Between the neighboring rolling bearings 126, spring elements 127A and 127B are provided for generating a preload to those rolling bearings 126. The spring elements 127A and 127B are in the form of, for example, compression coil springs. There are the spring element 127A for an inner ring to generate a preload to the inner ring of the rolling bearing 126 and a spring element 127B for an outer ring to generate a preload to the outer ring, and those are arranged alternately. With the preloads applied to the rolling bearings 126 through the spring elements 127A and 127B in this way, the inner wire 124 can be rotated at a high speed.

Figure 27:
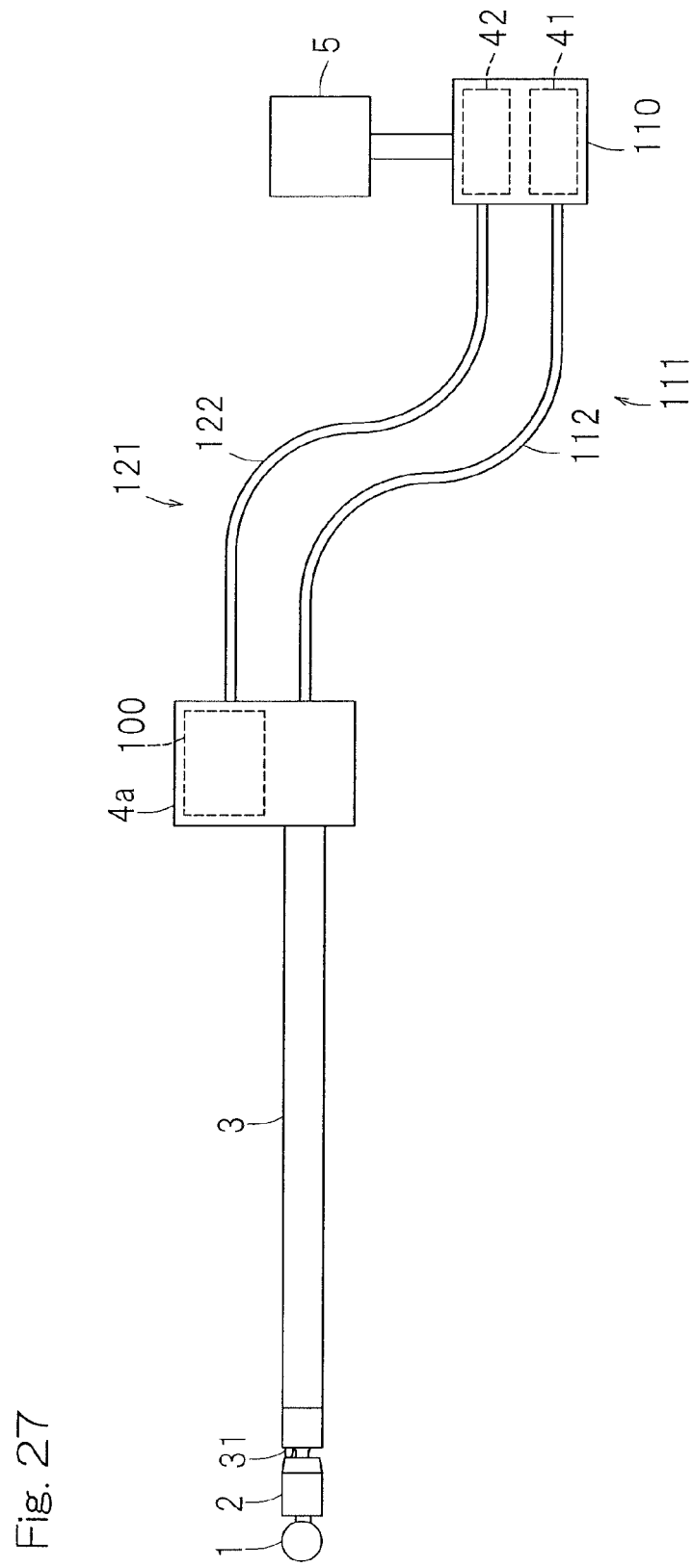
FIG. 27 is a diagram showing a schematic structure of the remote controlled actuator according to a seventh preferred embodiment of the present invention.
Figure 28:
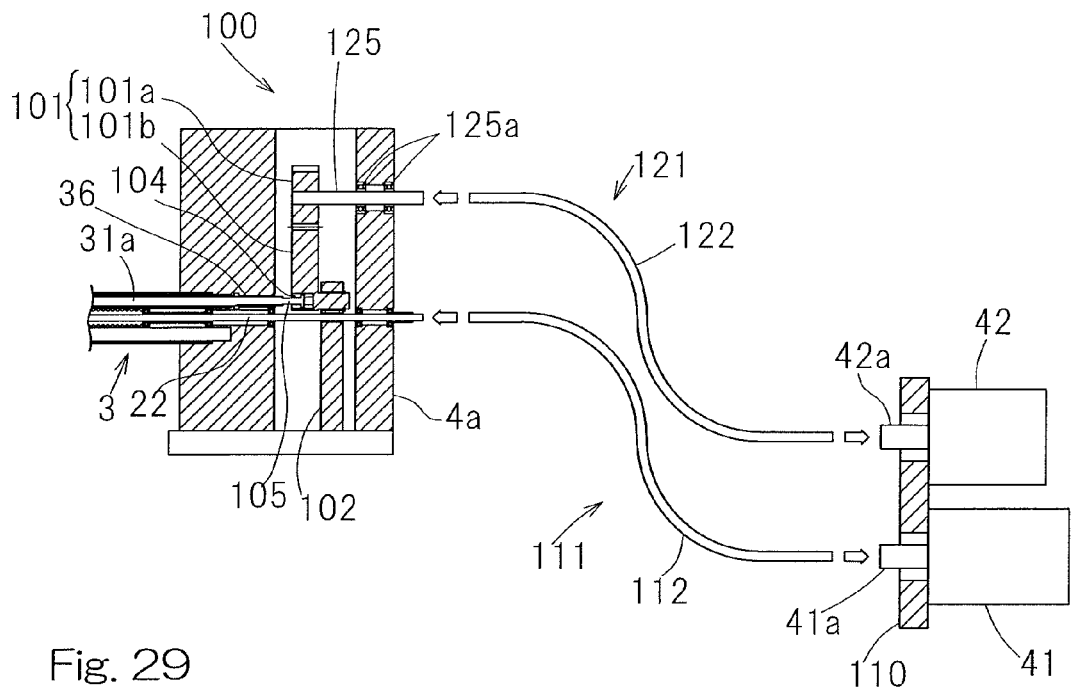
FIG. 28 is a side view showing, with a portion cut out, the structure of the tool rotation drive mechanism and the attitude altering drive mechanism of the remote controlled actuator.

As best shown in FIG. 27, a controller 5 for controlling the tool rotation drive source 41 and the attitude altering drive source 42 is connected with the drive source housing 110. The distal end member 2 and the spindle guide section 3 are of respective structures similar to those employed in any one of the previously described embodiments.

Although in describing the tool tip position detecting device for the remote controlled actuator reference has been made to that for the medical use, the present invention can be equally applied to the tool tip position detecting device for the remote controlled actuator for use in any application. By way of example, if the remote controlled actuator is used in performing a mechanical processing, a drilling process for drilling a curved hole and a cutting process to be performed at a site deep in the groove can be accomplished.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Tool
3 . . . Spindle guide
4 . . . Main body housing
5 . . . Remote controlled actuator
6 . . . Object to be processed
7A, 7B . . . Marker
8 . . . Marker detecting unit
9 . . . Computer
10 . . . Actuator main body
13 . . . Spindle
22 . . . Drive transmitting unit
31 . . . Attitude altering member
31a . . . Wire
36 . . . Screw mechanism
36a . . . Male screw portion
36b . . . Female screw portion
41 . . . Tool rotation drive source
42 . . . Attitude altering drive source
45 . . . Tool attitude detector
51 . . . Operator unit
51b . . . Attitude altering instrument (Attitude operating unit)
52 . . . Cable
53 . . . Tool tip position detecting device
54 . . . External force free position detector
55 . . . Corrector
55aA, 55aB . . . Type specific table
55b . . . Table selector
56 . . . Display unit
57 . . . Display information generator
60 . . . Strain sensor (Strain detector)
62X, 62Y . . . Strain detector
65, 72 . . . Correction determiner
66 . . . Alarming unit
67 . . . Medical electrosurgical knife (Instrument)
68 . . . Ultrasonic coagulation and dissection instrument (Instrument)
70 . . . Inspecting strain sensor
83 . . . Relative position storage unit
85 . . . Estimating unit
100 . . . Drive mechanism

What is claimed is:

1. A tool tip position detecting device for a remote controlled actuator, the remote controlled actuator including a spindle guide of an elongated shape, a main body housing connected with a base end of the spindle guide, a tool rotatably supported by a tip end of the spindle guide, a tool rotation drive source for rotating the tool through a drive transmission unit inserted within the spindle guide, and an operator unit for operating the tool rotation drive source, which device comprises:
    an external force free position detector for detecting a position and an attitude of the main body housing to detect a tip position of the tool when no external force is applied to the tool and the spindle guide, from a detection value thereof;
    a strain detector for detecting a strain of the spindle guide; and
    a corrector for correcting the tip position of the tool, detected by the external force free position detector, with the use of a detected strain value of the strain detector.

2. The tool tip position detecting device for the remote controlled actuator as claimed in claim 1, which device is capable of being used with a plurality of models of remote controlled actuators each utilizing the spindle guide of a different type, and
    in which the corrector includes a plurality of type specific tables, in which relations between detected strain values of the strain detector one for each types of the spindle guide and amount of corrections to be used in the correction are stored, and a table selector for selecting one of the type specific tables appropriate to a particular type of the spindle guide out from the plural type specific tables.

3. The tool tip position detecting device for the remote controlled actuator as claimed in claim 1, in which the external force free position detector includes
    a marker detecting unit for detecting a position and an attitude of a marker fitted to the main body housing,
    a relative position storage unit for storing relative positions of a tip of the tool relative to the marker, and an estimating unit for estimating the tip position of the tool from the position and the attitude of the marker, detected by the marker detecting unit, and the relative positions of the tip of the tool relative to the marker stored in the relative position storage unit.

4. The tool tip position detecting device for the remote controlled actuator as claimed in claim 1, in which the strain detector comprises a strain sensor fitted to the spindle guide.

5. The tool tip position detecting device for the remote controlled actuator as claimed in claim 4, in which the strain sensor is fitted to four or more axially same positions on an outer peripheral surface of the spindle guide in a fashion circumferentially spaced from each other.

6. The tool tip position detecting device for the remote controlled actuator as claimed in claim 4, in which the strain sensor is a strain gauge.

7. The tool tip position detecting device for the remote controlled actuator as claimed in claim 4, in which the strain detector is operable to transmit an output of the strain sensor in the form of an electrical signal to a control system portion of the tool tip position detecting device.

8. The tool tip position detecting device for the remote controlled actuator as claimed in claim 4, further comprising:
a correction determiner for receiving a signal indicative of an operating condition of an instrument, which is likely to form a noise generating source against the strain sensor, and for outputting an alarming command signal in the event that the signal indicates the instrument being operated; and
an alarming unit for outputting an alarm in response to the alarming command signal of the correction determiner.

9. The tool tip position detecting device for the remote controlled actuator as claimed in claim 4, further comprising:
an inspecting strain sensor separate from the strain sensor and insensible to an external force applied to the spindle guide;
a correction determiner for receiving an output value of the inspecting strain sensor or a processed value of the output value which has been applied with a predetermined signal processing and for outputting an alarming command signal in the event that the value thereof exceeds a predetermined threshold value; and
an alarming unit for outputting an alarm in response to the alarming command signal of the correction determiner.

10. The tool tip position detecting device for the remote controlled actuator as claimed in claim 8, in which in the event that the correction determiner outputs the alarming command signal, the corrector performs a correction with the use of a detected strain value of the strain detector immediately before the correction determiner outputs the alarming command signal.

11. The tool tip position detecting device for the remote controlled actuator as claimed in claim 1, further comprising:
a display unit for displaying one or both of an image and position information on a screen; and
a display information generator for displaying, on the screen, information on the tip position of the tool, which has been estimated by the external force free position detector and subsequently corrected by the corrector.

12. The tool tip position detecting device for the remote controlled actuator as claimed in claim 1, in which the spindle guide includes a spindle guide main body and a distal end member fitted to a tip of the spindle guide main body through a distal end member connecting structure for alteration in attitude, the distal end member rotatably supporting the tool, and
further comprising an attitude altering drive source for altering the attitude of the distal end member through an attitude altering member inserted within the spindle guide main body, and an attitude operating unit for operating the attitude altering drive source.

13. The tip position detecting device for the remote controlled actuator as claimed in claim 12, in which the distal end member rotatably supports a spindle for holding the tool, a rotation of the tool rotation drive source being transmitted to the spindle through the drive transmission unit and in which the attitude altering member has a flexibility and is inserted in a guide hole having its opposite end opening, the attitude of the distal end member being altered by selectively advancing or retracting the attitude altering member by means of a drive of the attitude altering drive source with the tip held in contact with the distal end member.

14. The tip position detecting device for the remote controlled actuator as claimed in claim 12, in which the distal end member rotatably supports a spindle for holding the tool, a rotation of the tool rotation drive source being transmitted to the spindle through the drive transmission unit and in which the attitude altering member is a wire and is inserted in a guide hole having its opposite end opening, the attitude of the distal end member being altered by selectively advancing or retracting the attitude altering member by means of a drive of the attitude altering drive source with the tip held in direct or indirect contact with the distal end member.

15. The tip position detecting device for the remote controlled actuator as claimed in claim 12, in which the distal end member rotatably supports a spindle for holding the tool, a rotation of the tool rotation drive source being transmitted to the spindle through the drive transmission unit and in which the attitude altering member is inserted in a guide hole having its opposite end opening, the attitude of the distal end member being altered by selectively advancing or retracting the attitude altering member by means of a drive of the attitude altering drive source with the tip held in direct or indirect contact with the distal end member, and
further comprising a drive mechanism section within the main body housing for transmitting an operation of the attitude altering drive source to the attitude altering member,
in which the drive mechanism section includes a screw mechanism having a male screw portion, formed in a base end of the attitude altering member, and a female screw portion fixed to the main body housing and meshed with the male screw portion,
in which the attitude altering drive source is comprised of a rotary actuator, the attitude altering member being selectively advanced or retracted by an action of the screw mechanism when the base end of the attitude altering member is rotated by the rotary actuator.

* * * * *

UNITED STATES PATENT AND TRADEMARK OFFICE
CERTIFICATE OF CORRECTION

PATENT NO. : 9,126,270 B2
APPLICATION NO. : 13/390600
DATED : September 8, 2015
INVENTOR(S) : Yukihiro Nishio et al.

It is certified that error appears in the above-identified patent and that said Letters Patent is hereby corrected as shown below:

In the claims

Claim 13, Column 30, Line 13

Delete "The" and insert --The tool--, therefor.

Claim 14, Column 30, Line 24

Delete "The" and insert --The tool--, therefor.

Claim 15, Column 30, Line 35

Delete "The" and insert --The tool--, therefor.

Signed and Sealed this
Twenty-ninth Day of December, 2015

Michelle K. Lee
*Director of the United States Patent and Trademark Office*